(12) United States Patent
Piotrowski et al.

(10) Patent No.: US 10,006,057 B2
(45) Date of Patent: Jun. 26, 2018

(54) RECOMBINANT YEAST HAVING ENHANCED GAMMA VALEROLACTONE TOLERANCE AND METHODS OF USE

(71) Applicants: Wisconsin Alumni Research Foundation, Madison, WI (US); Regents of the University of Minnesota, Minneapolis, MN (US)

(72) Inventors: Jeff S. Piotrowski, Madison, WI (US); Trey K. Sato, Madison, WI (US); Chad L. Myers, Arden Hills, MN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days. days.

(21) Appl. No.: 14/848,440

(22) Filed: Sep. 9, 2015

(65) Prior Publication Data

US 2016/0068869 A1    Mar. 10, 2016

Related U.S. Application Data

(60) Provisional application No. 62/048,458, filed on Sep. 10, 2014.

(51) Int. Cl.
| | | |
|---|---|---|
| *C12P 7/10* | (2006.01) | |
| *C12N 1/14* | (2006.01) | |
| *C12N 15/81* | (2006.01) | |

(52) U.S. Cl.
CPC ............... *C12P 7/10* (2013.01); *C12N 1/14* (2013.01); *C12N 15/81* (2013.01); *Y02E 50/16* (2013.01)

(58) Field of Classification Search
None
See application file for complete search history.

(56) References Cited

U.S. PATENT DOCUMENTS

2007/0141690 A1* 6/2007 Karhumaa ........... C12N 9/0006
435/161
2016/0040153 A1* 2/2016 Froehlich ................. C12N 9/92
435/161

OTHER PUBLICATIONS

Mukai et al., "PAD1 and FDC1 are essential for the decarboxylation of phenylacrylic acids in *Saccharomyces cerevisiae*", Journal of Bioscience and Bioengineering, vol. 109, No. 6, pp. 564-569, 2010.*

* cited by examiner

*Primary Examiner* — Richard C Ekstrom
(74) *Attorney, Agent, or Firm* — Boyle Fredrickson S.C.

(57) ABSTRACT

The present invention relates to materials and methods for the production of ethanol. More particularly, the present invention provides genetically modified strains of *Saccharomyces cerevisiae* having enhanced tolerance for gamma valerolactone (GVL) toxicity. Also provided are methods of using such genetically engineered yeast strains for improved GVL-mediated hydrolysis of lignocellulosic biomass for industrial-scale ethanol production.

22 Claims, 10 Drawing Sheets

FIGS. 1A-1B, CONTINUED
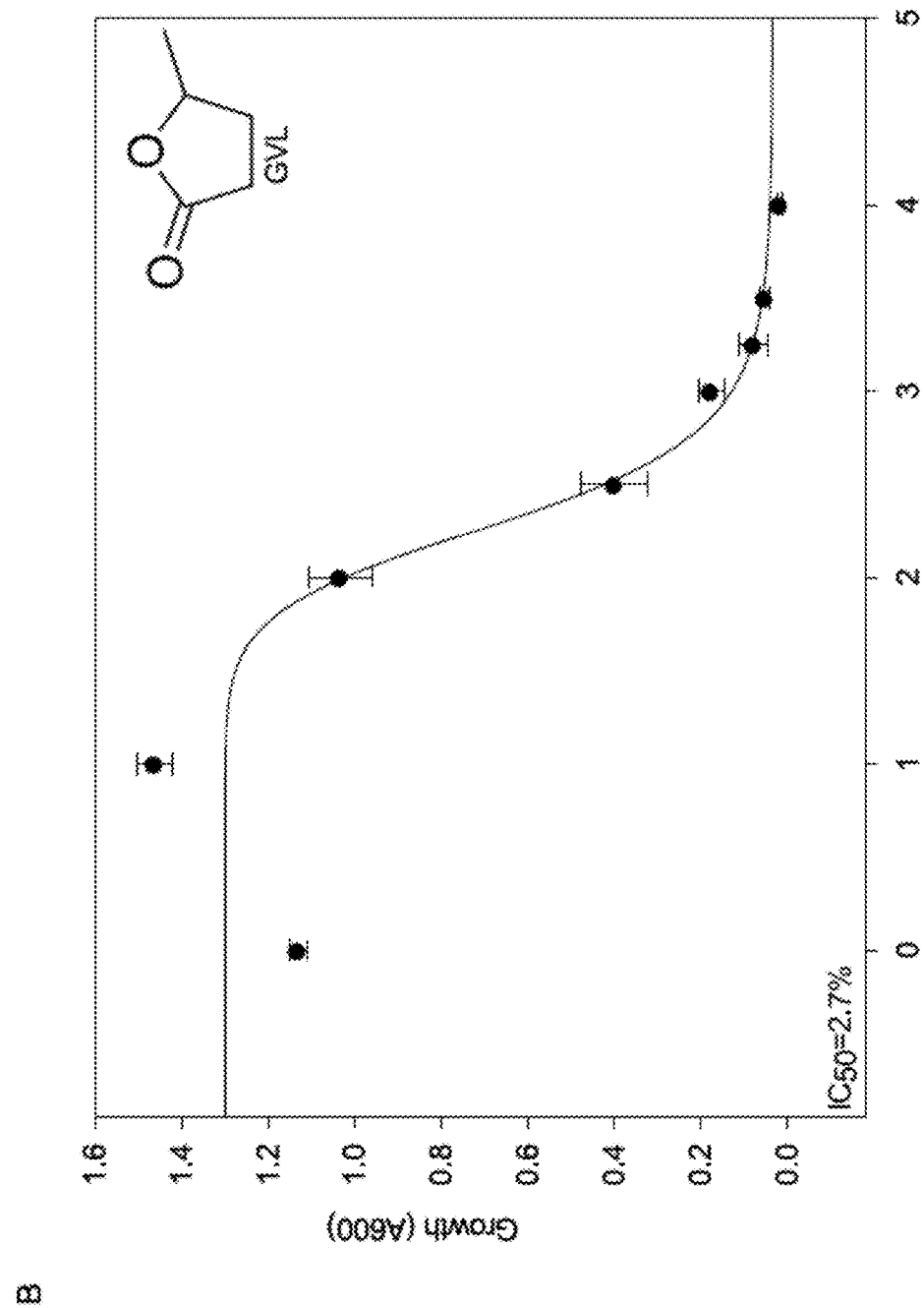

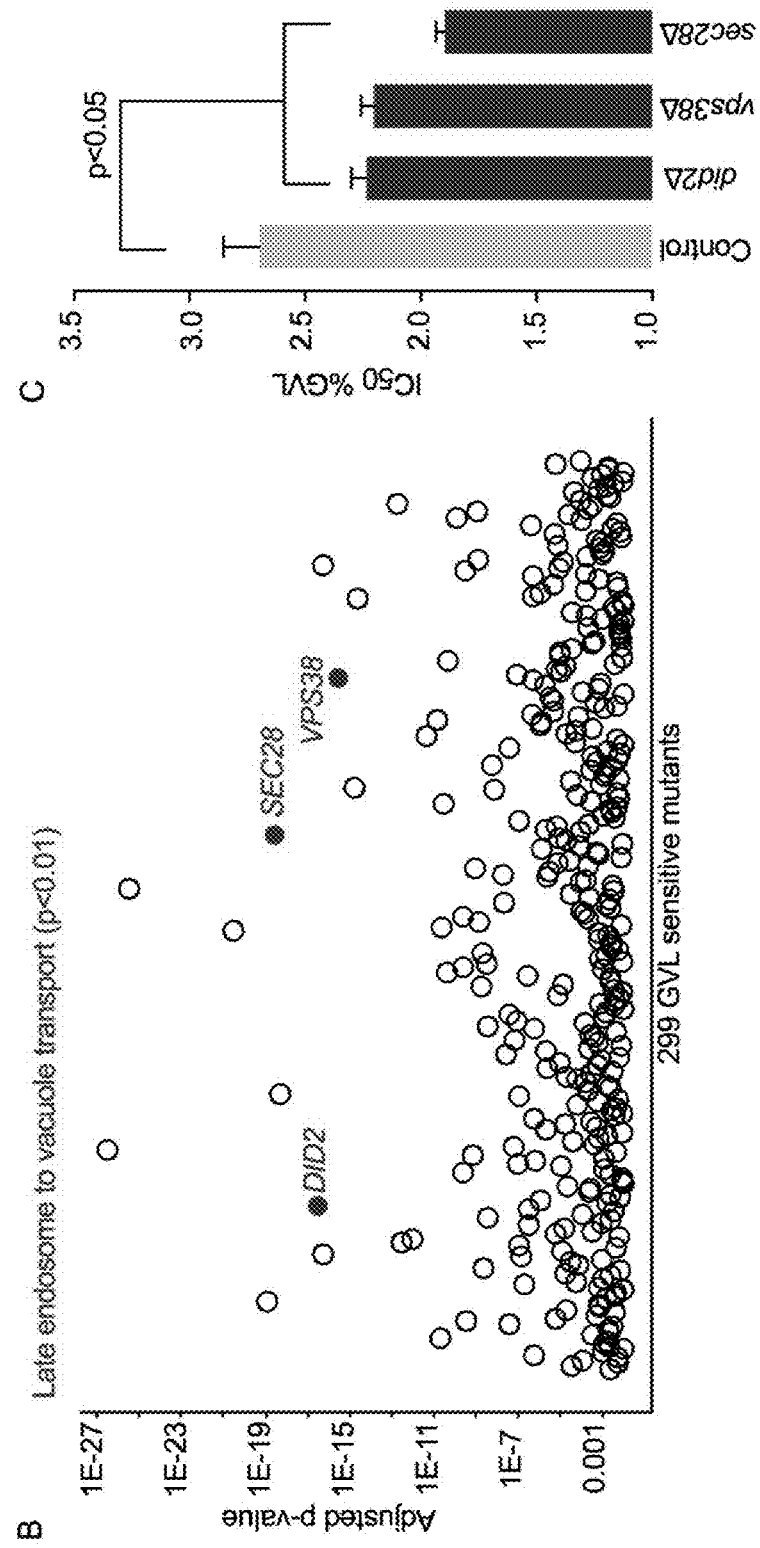
FIGS. 2A-2C, CONTINUED

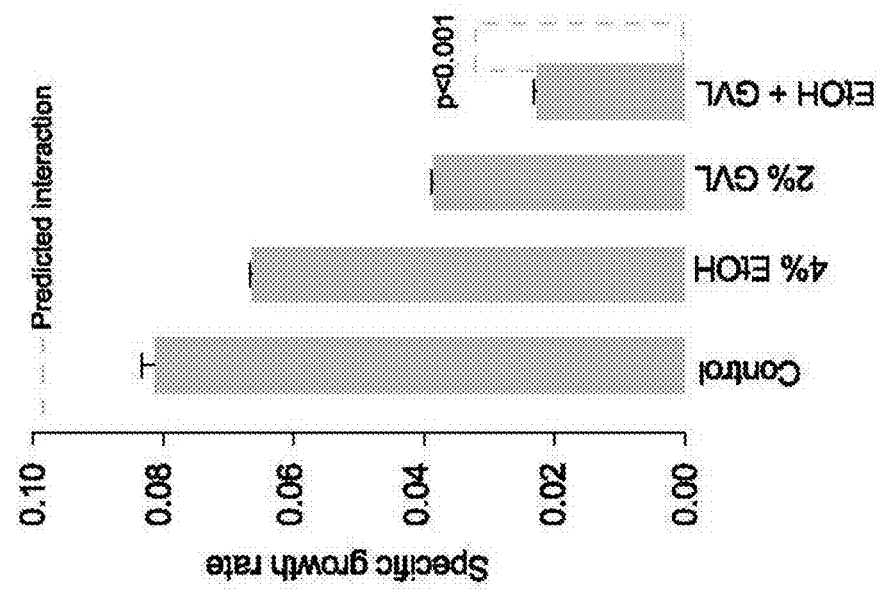
FIGS. 3A-3C, CONTINUED

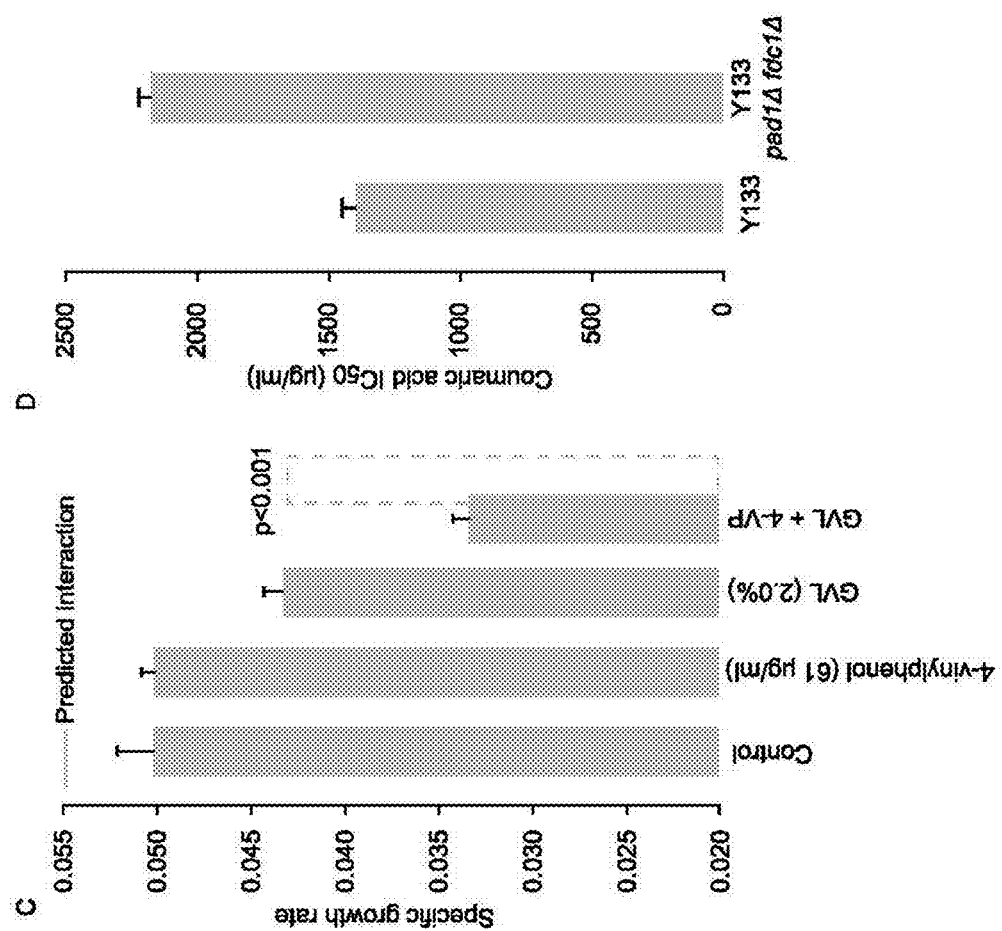
FIGS. 6A-6D, CONTINUED

SEQUENCE LISTING

<160> NUMBER OF SEQ ID NOS: 10

<210> SEQ ID NO 1
<211> LENGTH: 12012
<212> TYPE: DNA
<213> ORGANISM: Saccharomyces cerevisiae

```
<220> FEATURE:
<221> NAME/KEY: misc_feature
<223> OTHER INFORMATION: IRA2 coding sequence

<400> SEQUENCE: 1
ataccgatac tttccatacg cacttgattt agaggccggc tccactatcg agattgaaaa      60
tcagtatgga gaagtgatct tcttgggcaa gtatggctct tctccaatga ttaacttaag     120
gccaccttca agattatctg cagaaagttt acaggcatcc caagagccat tttactcctt     180
tcaaatcgat acgttaccag aactggatga ctctagtatc atcagtacat ccatttcact     240
ctcttatgac ggtgacgaca atgaaaaagc cctgacttgg gaagaactct aggtcaaact     300
ctatttttat acagcaatga gtaccttttc acatacacat aaatatatta aatataataa     360
atacaataaa tataaaataa ccccttttcga aactctttac ttcctaaggc ctctcattac     420
ttatcaccta gcatcatgct cttcatacat gccatctact ttcaaacgat atacggctaa     480
ccagaaaagt acggacaatc agggacgagc agggacatga cgccttccgc acagatccca     540
gagaaaagca gggaaacaag aaaataagaa acaagaaaa acagtagtta cccttgtaag     600
tgtcatccac aacagaacca atactcttac tcttccgctc attccccgca gaatgataga     660
actattctaa atcccccttgc cttgcttggc cttgacttgg gttgggactt ggacctctag     720
aaccgatgtg ccttcaaaca tcttagcgag ataagagtct gccattaatg catcgagcca     780
atatcttgga ctagtacgag gttcacgtag cctttcttgc acggaccag cgtcccaccc      840 caagttcttt gctatactga ccgccttaca catttttagtg tgattccaac ccaaagtagc     900
tcctcaaaaa gggtcacccg atcggtgaat caatccgcgg cgcagaaatg ttcgtagagc     960
tctcgtttct tctagaacgc tcccttgatg aaacgaaaat ttccatcaca ataaagctcg    1020
cacgcctttt tgaaaacccc aagctttgct gtgtcttctt gtgaaaagtt ttgcccaacg    1080
attatctatt ctacatataa ccggggagtt aagcacatcc tattgcccta cattctctcc    1140
gcttacttca ttgtctagag ctcctgggaa acaaaagacc gaaaaagcga aaacaaaatc    1200
agaacaaggc ttaagtactt tttcaccaat tgtagcaaac atttaaccac attttagcac    1260
actagcatat agcattgtcc tctgttattc gtttttgcttt tctcctttag tgttactttt    1320
cccccaacgt tacaccattt tttgatatca actaaactgt atacattatc tttcttcagg    1380
gagaagcatg tccagcccca ctaagaataa gaagaaagaa cacgggaccg attccaagtc    1440
atcccgcatg actcggacgt tggttaatca tattctttt gaaagaattc tcccgatcct    1500
tccggtggag tctaatctaa gtacctattc ggaagtggaa gagtattcct cattcatttc    1560
atgcagatct gtgctcatta acgttaccgt ttcccgagat gcaaatgcta tggtggaagg    1620 cacccttggag ttgatagaat cgcttcttca agggcacgaa atcatttcag ataagggtag    1680
cagtgacgtt attgaatcaa tactgattat actaagattg ttaagtgatg cgctagagta    1740
taattggcaa aatcaagaaa gccttcatta caacgacatt tcgactcacg tagaacatga    1800
ccaagaacag aagtacagac caaagcttaa cagtattctg cccgactact cgtcgactca    1860
ttccaatggc aacaaacact ttttccacca gagcaaacct caggcactga taccggaact    1920
ggcatcgaaa ttgcttgaga gttgcgcgaa gttgaagttc aatacaagaa ctttgcaaat    1980
tttacaaaat atgatcagtc atgttcatgg aaacattcta acgactttga gttcctcgat    2040
tcttccccgc cacaaatcct atctgacaag gcacaaccat ccttctcatt gtaaaatgat    2100
tgactctact ctaggccata ttctccgatt tgtagcggct tccaatccgt ccgagtattt    2160
tgaatttatc agaaagagtg tgcaagtgcc cgtaacacag acacacacgc attcacactc    2220
```

```
ccattcacac tctttgccat cttccgttta taacagcata gtgccccact ttgatctttt      2280
cagcttcatc tatttaagca agcataattt taagaaatac ttggaactca tcaaaaactt      2340
atcggtgacg ttaaggaaaa cgatttatca ttgcctactt ttgcattaca gcgccaaagc      2400
aataatgttt tggataatgg ctaggcctgc ggaatattat gaactcttca acttattaaa      2460
agataataac aatgaacact cgaaatcctt aaacacgtta aaccatacac ttttcgagga      2520
gatccattcg acttttaatg tgaatagcat gataaccacc aatcaaaatg ctcatcaagg      2580
ctcatcttcc ccttcgtcct cctcgccatc gtcaccacct agctcatcat catcggataa      2640
caacaatcaa aacataatag caaaatcctt aagtcgtcag ctttctcacc accagtcata      2700
cattcaacag cagtctgaaa gaaaactaca ttcttcatgg actacaaact ctcaatcctc      2760
tacttcactg tcatcttcaa cgtctaattc aacaacaact gatttctcta ctcacactca      2820
accaggagaa tatgacccctt ccttaccaga tactcccacg atgtctaaca tcactattag      2880
tgcatcttca ttattatctc aaactccaac tccaacaaca caattgcaac agcggttgaa      2940
ctcagcagct gcagccgccg ccgcagctgc ttcaccatcg aattccaccc caactggata      3000
cacagcagag caacaaagtc gcgcttcata cgatgcacac aaaactggcc atactggtaa      3060
ggattatgac gaacattttt tgtctgtcac tcgtttggat aatgttttgg agttatacac      3120
gcactttgat gatactgagg tactaccaca cacatccgta ctgaagtttt taactacttt      3180
gacaatgttc gatattgacc tttttaatga attaaacgct acatcattca aatatattcc      3240
tgattgtact atgcatcgtc caaaagaaag aacaagttct ttcaataata ctgcacacga      3300
gacaggttcc gaaaagactt cgggtataaa acatattaca caaggcttaa agaaattaac      3360
ttctttacct tcctcaacca aaaaaactgt aaaatttgtg aagatgttgc taagaaattt      3420
aaatgggaat caagctgtat cagatgttgc cctcttagat acaatgaggg ccttactatc      3480
attctttaca atgacttctg cggtcttttct cgtggataga aacttaccct cagtactttt      3540
tgccaagaga ctcatcccca taatggggac aaatttaagc gtcggtcaag actgaaattc      3600
aaaaataaat aacagtttga tggtttgttt gaaaaaaaac tccaccacgt ttgttcaatt      3660
acaattaata ttcttctctt cagctattca attcgatcat gaattattac tggcacgtct      3720
gagcatcgat acaatggcca acaatttaaa catgcagaag ctatgccttt atactgaagg      3780
attcaggata ttcttcgaca taccaagtaa gaaggaattg cggaaggcaa ttgcggttaa      3840
aatttctaaa ttttcaaaa cattattctc cattatagca gatattcttt tacaagaatt      3900
tccgtatttt gatgagcaaa tcaccgacat agttgcttcc attcttgacg gtacaattat      3960
caatgagtat ggtacgaaga acatttcaa ggggagctca ccctctttat gttcgacaac      4020
ccggtcaaga tcaggatcta catctcaaag ttcaatgaca ccagtttctc cgctgggact      4080
ggatactgat atatgtccaa tgaacaccct gtctttagtt ggttcaagta cttcaagaaa      4140
ttctgacaac gttaattcat taaacagttc accaaagaac ttgtcttctg atccatactt      4200
gtcacatctt gtggccccaa gagcgcgtca tgctttaggt gggccatcta gtattataag      4260
gaataaaata ccgactacat tgacttcacc tccaggaacg gaaaaatctt caccagtaca      4320
acgtccgcaa acggaaagca tcagtgccac accaatggcc ataacaaatt ctactccatt      4380
atcgtcggca gcattcggaa ttcgatcgcc tttgcagaaa ataagaacga ggcgttattc      4440
cgatgaaagt ttaggaaaat tcatgaaatc aacaaataat tacattcaag aacatttgat      4500
accaaaagat ttgaatgaag caactcttca agatgctaga agaataatga ttaatatttt      4560 cagtatttt aagagaccga atagttactt catcattcct cacaatataa actcgaattt      4620
```

```
acaatgggtt tcgcaggatt ttagaaatat tatgaaaccg attttcgtcg ccatcgtaag    4680
tccggatgta gatttacaga atactgctca atcattcatg gataccttat tatcgaatgt    4740
tattacttat ggtgaatcag atgagaatat cagtattgaa gggtatcatc ttctttgcag    4800
ttacactgta acattatttg caatgggcct tttcgatttg aaaattaata atgaaaagcg    4860
tcaaattctc ttggatataa ctgtcaagtt tatgaaggtt agatcacatt tagcagggat    4920
cgcggaggcc tcacaccaca tggaatacat aagtgattct gaaaaactca cctttccgct    4980
gattatgggg actgttggta gggccctatt tgtttcatta tactctagtc aacaaaaaat    5040
tgaaaagact ttaaagattg cttacacaga gtatctttct gcaatcaatt ttcatgagag    5100
gaatattgat gatgctgata aaacttgggt tcataatatt gagtttgtag aagcgatgtg    5160
tcatgacaac tacacaactt ctggttcaat tgctttccaa aggaggacaa gaaataatat    5220
tttacgattt gctactattc ctaacgctat cttacttgat tctatgagga tgatctataa    5280
gaagtggcat acttacacac acagtaaaag tttagaaaaa caagaacgga acgacttcag    5340
aaatttcgcg ggtattttag cctctttgtc gggtatccta ttcatcaata aaaagatatt    5400
gcaagaaatg tatccatacc tactcgacac cgtttcagaa ttgaaaaaaa atatagactc    5460
ttttatctca aaacaatgcc aatggttaaa ctatccggat ttattaacga gagaaaattc    5520
aagagatatt ctaagtgtag aactgcatcc tttgtctttt aacttacttt ttaataattt    5580
gaggctcaag ttaaaagaac ttgcttgttc agacttatca ataccagaaa atgaaagttc    5640
ctatgtttta ttagaacaaa taatcaaaat gctgcggaca atcctaggtc gtgatgatga    5700
caattatgta atgatgcttt tttccacaga gattgtagat cttattgatt tattgacaga    5760
tgaaataaaa aaaataccag cctattgtcc aaaatatctc aaggcaatta ttcaaatgac    5820
caaaatgttc agtgccttgc agcactcaga ggttaattta ggtgtcaaaa atcattttca    5880
cgttaaaaat aaatggttga ggcaaatcac tgattggttt caagtgagta ttgcgagaga    5940
gtacgatttc gaaaacttgt caaaacctct aaaagaaatg gatttggtaa aaagagacat    6000
ggatattcta tacatagata cggcaatcga agcttcaacc gctattgcgt acctcacgag    6060
acatactttc ttagagattc cacctgccgc gtcagatccc gaactatctc gatctaggtc    6120
tgtgatattt gggttttatt tcaacatctt aatgaaaggc cttgaaaaaa gtagtgatcg    6180
tgacaattac ccagtattct tgaggcacaa aatgagtgtc ctcaacgaca atgtaatact    6240
ttcattaaca aatctttcaa acaccaatgt tgatgcgagt ttgcagttca ccttaccgat    6300
gggctattcc ggaaatcgaa acattaggaa tgcattttg gaggtcttca ttaatatcgt    6360
tacgaactat cggacataca cggctaaaac tgaccttgga aaattagagg cagcagacaa    6420
atttttgcga tatacgattg aacatcccca gctatcgtcc tttggagcag cggttttgtcc    6480 cgctagcgat attgatgctt atgctgctgg cttaataaat gcatttgaaa cgaggaatgc    6540
cacccacatt gtagtggcac agttgattaa aaatgaaatt gaaaatctt ccagacctac    6600 ggatatcctt agaagaaata gctgtgctac gagatcatta tctatgctag ccaggtccaa    6660
gggtaacgaa tatttgattc gcactttgca accattacta aaaaaaatta tccagaacag    6720
agattttttt gaaattgaga aactaaaacc ggaagattca gatgctgaac gtcaaataga    6780
gctcttcgtt aaatacatga atgaattatt ggaatccata tccaactccg tatcttattt    6840 tcccctcct ttattttata tttgccaaaa catttataaa gttgcgtgtg aaaaatttcc    6900
ggatcacgca attatcgccg ctgggtcttt cgtgttttta cggttttttt gtcctgcttt    6960
agtcagccct gattctgaaa atatcataga tatttctcac ttgagcgaaa agcgtacctt    7020
```

```
catcagcttg gctaaagtta ccaaaatat tgccaatggc tcagaaaatt tctccagatg      7080
gccagctttg tgttcccaaa aggatttct taaggaatgt agcgatagaa ttttcagatt      7140
cctagctgaa ctttgtagaa cagatcgcac gatagacatc caagtgagaa cagacccaac    7200
gccaattgca tttgactatc aattccttca ttcctttgtt taccttacg gtcttgaggt     7260 gagaaggaat gtgctaaatg aagcaaaaca tgatgatggt gacattgatg gtgacgattt    7320
ctataagacc acatttttac ttattgatga tgttcttggc caattaggcc aacctaaaat    7380
ggaattttcc aatgaaatac caatatacat aagagaacat atggacgact atccggaact    7440
gtatgagttc atgaataggc acgcgttcag aaacattgag acttcaacag cgtacagccc    7500
aagcgttcac gagtccacct caagtgaagg cattccaatt attacgttaa caatgtcaaa    7560
tttctcagac agacatgtgg acattgatac agttgcttac aagttcttgc aaatttatgc    7620
tcgaatctgg accaccaaac actgtttaat aatcgactgt acagaatttg acgagggagg    7680
gcttgatatg aggaaattta tttctttggt tatgggacta ttaccagaag ttgcacccaa    7740
aaattgtata ggctgttact actttaacgt aaacgagaca tttatggata attatggaaa    7800
atgtttggac aaagacaacg tatatgtttc ctcgaaaatt cctcattatt tcattaatag    7860
taactctgat gaaggactta tgaaatctgt gggtataact ggacagggt tgaaggttct     7920 gcaagatatt cgtgtctctc tgcatgatat cacgctttat gacgaaaaa gaaatagatt     7980 tacgccggta tcgttgaaaa taggcgatat ttactttcaa gtcttgcatg aaactcctag    8040
gcaatataaa ataagggaca tgggtacttt attcgacgta aaattcaatg atgtctacga    8100
aattagccga atatttgaag tacatgttc gtcaataact ggagtggcag ctgaatttac     8160
agtaactttt caggacgaga gaaggttgat ttttagtagt ccgaaatacc ttgaaattgt    8220
gaagatgttc tattacgcac agatccggtt agaaagtgaa tatgaaatgg ataataattc    8280
gagtacctcc tccccaaatt caaacaacaa ggacaaacag cagaaagaga gaacaaaact    8340
attgtgccac ctactgttag tatctcttat tggtctgttt gatgagagta aaaaaatgaa    8400
aaacagttcg tataacctaa tagctgccac tgaggcgtca tttggttga actttggctc     8460 ccattttcat cgctctcccg aggtgtacgt ccccgaagat actacaacat tttaggtgt     8520 tattggaaag tctcttgcag agtctaatcc agaactcaca gcctatatgt ttatctatgt    8580
tttggaggca ttgaagaaca acgtaattcc tcacgtttac atccctcata ccatttgcgg    8640
tttgtcttat tggatcccta atttataccaa acatgtgtat ttggctgatg atgaagaagg    8700
ccccgaaaac atatctcaca ttttccgaat tcttatcagg ctctctgtga gagagactga    8760
ctttaaagcc gtatacatgc aatatgtttg gttgctactt ttagatgatg gccgcttaac    8820
tgacattatc gttgatgaag ttattaatca tgcgttagaa agagactccg aaaaccgcga    8880
ttggaagaaa acaatatcgt tactgactgt cctacccact actgaggttg ctaataatat    8940
tattcaaaaa atattggcaa aaattagatc attttaccg tcattgaagt tagaagctat     9000
gacccaaagt tggtctgaac taacaatatt agttaagata agcatccacg ttttttttga    9060
aacttctttg ctggtacaga tgtacttacc agagatcctg tttatcgtat ccttattaat    9120
tgatgttggt ccaagggaac tcagatcatc actacaccag ctattaatga atgtatgcca    9180
ttccttggct attaactcag ctttaccaca agatcataga aataatctag atgaaataag    9240
tgatatattt gcacatcaaa aggtgaagtt tatgttgggg ttcagcgagg acaaaggacg    9300
aattttacag atttttagcg cttcttcttt tgcaagcaag tttaatattc tggatttctt    9360
catcaataat atattattgc tgatggaata ttcttcaacg tacgaagcaa acgtgtggaa    9420
```

```
gacaagatac aagaaatatg tcttggaatc tgtgtttaca agtaattctt ttctttcggc    9480
acgttcaatc atgattgttg gtataatggg taaatcttac ataactgaag ggttatgcaa    9540
ggctatgtta attgaaacca tgaaagttat cgccgaacca aagattactg acgagcatct    9600
tttcttagcc atatctcata ttttttactta ttccaaaatt gttgaaggtt tggatcccaa    9660
ccttgactta atgaagcact atttttggtt ttcaacactc ttccttgaat cacgtcaccc    9720 gataatttt gagggtgccc ttctcttgt gtcaaactgt ataaggcgcc tatacatggc    9780
ccagtttgaa aatgaaagcg aaacatcatt gataagtact ttacttaagg ggagaaagtt    9840
tgctcatacc ttttaagca agatagagaa tcttagtggt attgtttgga atgaagataa    9900
ttttacacac attctgattt tcatcattaa taaaggacta tccaatcctt tcattaagag    9960
tacggctttt gatttcttga agatgatgtt tagaaactcc tactttgagc atcaaatcaa   10020
tcagaaatct gatcattatt tgtgctatat gttcctattg tattttgttt taaactgcaa   10080
tcaatttgag aactttttag gtgacgttga ttttgaagga gaaatggtta acattgaaaa   10140
caagaacacc attcctaaaa ttttgttaga gtggttgagt tcggataacg aaaatgcaaa   10200
cattaccctc tatcaaggtg cgatactgtt caaatgttca gttacggatg aaccaagtag   10260
atttaggttt gcgttgatta ttaggcatct attgacaaag aaacccattt gtgcattgcg   10320
tttttacagt gttattcgta acgaaataag aaaaatatca gcatttgagc aaaattcgga   10380
ttgtgttcca cttgctttcg atattttaaa cttattagtg acgcattcag agtctaattc   10440
gttagaaaaa cttcacgaag aatccattga acgtctaacc aaaagaggtt tatcgattgt   10500
gacttcttct ggtatatttg cgaagaactc cgacatgatg atacctttag atgtaaaacc   10560
tgaagatatc tatgaacgta agagaataat gacaatgatt ttatcaagga tgtcatgttc   10620
tgcttagagg tgttacataa actaatgaaa gaaatatcaa tatctatctg taagcatgaa   10680
tgtacatatc tcatgttagg gttttcttat cgctaatttt tcgcaatttg ttacgtgggt   10740
tgcttttata cagctacaat ttttatatat tctatcgtgt aatgaatggc tcagtaaatt   10800
caagcgccac atagactaat gtacatacca atgcatttta attgtaagaa taaaagggc   10860 cattcatcta ccgtcttagt tgaaagtgtt tctgtgaatt ttttcaaatt ccgtttttc   10920 cttttatat aatagcatgg tggcacgagc atcttcgact gaagaatgct caccttcttg   10980
aatggaaatt tttaaaacct ccctggttaa tttcttaag ctgggtgttt tacccttagc   11040
atacaacttc ctgaatggga ggtgtcttga agtgtccctg agtagtgact ttgggtggga   11100
taacatcaat gcttcgagat catgcttaa agcgtgccct acaagaattc taccttccag   11160
aatatccgca gtctttttt gagcttcttt gaatgtaatg gcattttca tatgctctgg   11220 tttaatacca ctaacccaag ttctccattc tacaactttc tctcttggct taacaaattc   11280
atcgaggacg acatgtccaa aataatttac gattgatatt ctagctaacg cagactcttt   11340
accctcggga ccaacgccta caaattcaca atccatggcg atgtatttcc caattcttt   11400 actcttatta ctattaatac gagtatcttc cgaaataccc acttttactg gctctttaat   11460
agtagtacta gtatttgctt tatttgggtt gaattcaaac acttttccct cgagcttgtc   11520
tttctcatgc ttactaatct ccttgttcat gttatatacc atgtccataa ttttactgcc   11580
gtttttgcgc tttcgagggg catattgggt tgtactactg acatttactg ttttgctaac   11640
tttcttaacg tttctgattt tcctatttga ttgcttattc tttccattgg aggtaggatt   11700
gctttcggag gctaatagtg cctgccagtt tgaagagaga gccattaaaa ctgtacgcta   11760
tctactttat taaatctgta aacgtctatg aagcctctag aaccaggctt taaatggatt   11820
```

-continued

```
gtggttgcga tgaggttagt ttaacttttg aaatttttct ttttttagc cgaccttaca    11880 tatcagcccg cgtcaaaaaa tatacggtat aataattctc aatagataca ggctactgaa    11940
caggaaaact aaataaaaca gtgtttgtaa aacccccacc acaccataat aagacgataa    12000
tggacacggt ga                                                         12012
```

<210> SEQ ID NO 2
<211> LENGTH: 3079
<212> TYPE: PRT
<213> ORGANISM: Saccharomyces cerevisiae

<400> SEQUENCE: 2

```
Met Ser Gln Pro Thr Lys Asn Lys Lys Glu His Gly Thr Asp Ser
1               5                   10                  15

Lys Ser Ser Arg Met Thr Arg Thr Leu Val Asn His Ile Leu Phe Glu
            20                  25                  30

Arg Ile Leu Pro Ile Leu Pro Val Glu Ser Asn Leu Ser Thr Tyr Ser
        35                  40                  45

Glu Val Glu Glu Tyr Ser Ser Phe Ile Ser Cys Arg Ser Val Leu Ile
    50                  55                  60

Asn Val Thr Val Ser Arg Asp Ala Asn Ala Met Val Glu Gly Thr Leu
65                  70                  75                  80

Glu Leu Ile Glu Ser Leu Leu Gln Gly His Glu Ile Ile Ser Asp Lys
                85                  90                  95

Gly Ser Ser Asp Val Ile Glu Ser Ile Leu Ile Ile Leu Arg Leu Leu
            100                 105                 110

Ser Asp Ala Leu Glu Tyr Asn Trp Gln Asn Gln Glu Ser Leu His Tyr
        115                 120                 125

Asn Asp Ile Ser Thr His Val Glu His Asp Gln Glu Gln Lys Tyr Arg
    130                 135                 140

Pro Lys Leu Asn Ser Ile Leu Pro Asp Tyr Ser Ser Thr His Ser Asn
145                 150                 155                 160

Gly Asn Lys His Phe Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
            180                 185                 190

Thr Arg Thr Leu Gln Ile Leu Gln Asn Met Ile Ser His Val His Gly
        195                 200                 205

Asn Ile Leu Thr Thr Leu Ser Ser Ser Ile Leu Pro Arg His Lys Ser
    210                 215                 220

Tyr Leu Thr Arg His Asn His Pro Ser His Cys Lys Met Ile Asp Ser
225                 230                 235                 240

Thr Leu Gly His Ile Leu Arg Phe Val Ala Ala Ser Asn Pro Ser Glu
                245                 250                 255

Tyr Phe Glu Phe Ile Arg Lys Ser Val Gln Val Pro Val Thr Gln Thr
            260                 265                 270

His Thr His Ser His Ser His Ser Leu Pro Ser Ser Val Tyr
        275                 280                 285

Asn Ser Ile Val Pro His Phe Asp Leu Phe Ser Phe Tyr Leu Ser
    290                 295                 300

Lys His Asn Phe Lys Lys Tyr Leu Glu Leu Ile Lys Asn Leu Ser Val
305                 310                 315                 320

Thr Leu Arg Lys Thr Ile Tyr His Cys Leu Leu Leu His Tyr Ser Ala
                325                 330                 335
```

```
Lys Ala Ile Met Phe Trp Ile Met Ala Arg Pro Ala Glu Tyr Tyr Glu
                340                 345                 350

Leu Phe Asn Leu Leu Lys Asp Asn Asn Glu His Ser Lys Ser Leu
            355                 360                 365

Asn Thr Leu Asn His Thr Leu Phe Glu Glu Ile His Ser Thr Phe Asn
    370                 375                 380

Val Asn Ser Met Ile Thr Thr Asn Gln Asn Ala His Gln Gly Ser Ser
385                 390                 395                 400

Ser Pro Ser Ser Ser Pro Ser Ser Pro Pro Ser Ser Ser Ser Ser
                405                 410                 415

Asp Asn Asn Asn Gln Asn Ile Ile Ala Lys Ser Leu Ser Arg Gln Leu
            420                 425                 430

Ser His His Gln Ser Tyr Ile Gln Gln Gln Ser Glu Arg Lys Leu His
            435                 440                 445

Ser Ser Trp Thr Thr Asn Ser Gln Ser Ser Thr Ser Leu Ser Ser Ser
        450                 455                 460

Thr Ser Asn Ser Thr Thr Thr Asp Phe Ser Thr His Thr Gln Pro Gly
465                 470                 475                 480

Glu Tyr Asp Pro Ser Leu Pro Asp Thr Pro Thr Met Ser Asn Ile Thr
                485                 490                 495

Ile Ser Ala Ser Ser Leu Leu Ser Gln Thr Pro Thr Pro Thr Thr Gln
            500                 505                 510

Leu Gln Gln Arg Leu Asn Ser Ala Ala Ala Ala Ala Ala Ala Ala
        515                 520                 525

Ser Pro Ser Asn Ser Thr Pro Thr Gly Tyr Thr Ala Glu Gln Gln Ser
    530                 535                 540

Arg Ala Ser Tyr Asp Ala His Lys Thr Gly Thr Gly Lys Asp Tyr
545                 550                 555                 560

Asp Glu His Phe Leu Ser Val Thr Arg Leu Asp Asn Val Leu Glu Leu
                565                 570                 575

Tyr Thr His Phe Asp Asp Thr Glu Val Leu Pro His Thr Ser Val Leu
            580                 585                 590

Lys Phe Leu Thr Thr Leu Thr Met Phe Asp Ile Asp Leu Phe Asn Glu
        595                 600                 605

Leu Asn Ala Thr Ser Phe Lys Tyr Ile Pro Asp Cys Thr Met His Arg
    610                 615                 620

Pro Lys Glu Arg Thr Ser Ser Phe Asn Asn Thr Ala His Glu Thr Gly
625                 630                 635                 640

Ser Glu Lys Thr Ser Gly Ile Lys His Ile Thr Gln Gly Leu Lys Lys
                645                 650                 655

Leu Thr Ser Leu Pro Ser Ser Thr Lys Lys Thr Val Lys Phe Val Lys
            660                 665                 670

Met Leu Leu Arg Asn Leu Asn Gly Asn Gln Ala Val Ser Asp Val Ala
        675                 680                 685

Leu Leu Asp Thr Met Arg Ala Leu Leu Ser Phe Phe Thr Met Thr Ser
    690                 695                 700

Ala Val Phe Leu Val Asp Arg Asn Leu Pro Ser Val Leu Phe Ala Lys
705                 710                 715                 720

Arg Leu Ile Pro Ile Met Gly Thr Asn Leu Ser Val Gly Gln Asp Trp
                725                 730                 735

Asn Ser Lys Ile Asn Asn Ser Leu Met Val Cys Leu Lys Lys Asn Ser
            740                 745                 750
```

-continued

```
Thr Thr Phe Val Gln Leu Gln Leu Ile Phe Phe Ser Ala Ile Gln
        755                 760                 765

Phe Asp His Glu Leu Leu Ala Arg Leu Ser Ile Asp Thr Met Ala
    770                 775                 780

Asn Asn Leu Asn Met Gln Lys Leu Cys Leu Tyr Thr Glu Gly Phe Arg
785                 790                 795                 800

Ile Phe Phe Asp Ile Pro Ser Lys Lys Glu Leu Arg Lys Ala Ile Ala
                805                 810                 815

Val Lys Ile Ser Lys Phe Phe Lys Thr Leu Phe Ser Ile Ile Ala Asp
            820                 825                 830

Ile Leu Leu Gln Glu Phe Pro Tyr Phe Asp Glu Gln Ile Thr Asp Ile
        835                 840                 845

Val Ala Ser Ile Leu Asp Gly Thr Ile Ile Asn Glu Tyr Gly Thr Lys
850                 855                 860

Lys His Phe Lys Gly Ser Ser Pro Ser Leu Cys Ser Thr Thr Arg Ser
865                 870                 875                 880

Arg Ser Gly Ser Thr Ser Gln Ser Ser Met Thr Pro Val Ser Pro Leu
                885                 890                 895

Gly Leu Asp Thr Asp Ile Cys Pro Met Asn Thr Leu Ser Leu Val Gly
            900                 905                 910

Ser Ser Thr Ser Arg Asn Ser Asp Asn Val Asn Ser Leu Asn Ser Ser
        915                 920                 925

Pro Lys Asn Leu Ser Ser Asp Pro Tyr Leu Ser His Leu Val Ala Pro
    930                 935                 940

Arg Ala Arg His Ala Leu Gly Gly Pro Ser Ser Ile Ile Arg Asn Lys
945                 950                 955                 960

Ile Pro Thr Thr Leu Thr Ser Pro Pro Gly Thr Glu Lys Ser Ser Pro
                965                 970                 975

Val Gln Arg Pro Gln Thr Glu Ser Ile Ser Ala Thr Pro Met Ala Ile
            980                 985                 990

Thr Asn Ser Thr Pro Leu Ser Ser  Ala Ala Phe Gly Ile  Arg Ser Pro
        995                 1000                1005

Leu Gln Lys Ile Arg Thr Arg  Arg Tyr Ser Asp Glu  Ser Leu Gly
    1010            1015                1020

Lys Phe Met Lys Ser Thr Asn  Asn Tyr Ile Gln Glu  His Leu Ile
    1025            1030                1035

Pro Lys Asp Leu Asn Glu Ala  Thr Leu Gln Asp Ala  Arg Arg Ile
    1040            1045                1050

Met Ile Asn Ile Phe Ser Ile  Phe Lys Arg Pro Asn  Ser Tyr Phe
    1055            1060                1065

Ile Ile Pro His Asn Ile Asn  Ser Asn Leu Gln Trp  Val Ser Gln
    1070            1075                1080

Asp Phe Arg Asn Ile Met Lys  Pro Ile Phe Val Ala  Ile Val Ser
    1085            1090                1095

Pro Asp Val Asp Leu Gln Asn  Thr Ala Gln Ser Phe  Met Asp Thr
    1100            1105                1110

Leu Leu Ser Asn Val Ile Thr  Tyr Gly Glu Ser Asp  Glu Asn Ile
    1115            1120                1125

Ser Ile Glu Gly Tyr His Leu  Leu Cys Ser Tyr Thr  Val Thr Leu
    1130            1135                1140

Phe Ala Met Gly Leu Phe Asp  Leu Lys Ile Asn Asn  Glu Lys Arg
    1145            1150                1155
```

```
Gln Ile Leu Leu Asp Ile Thr Val Lys Phe Met Lys Val Arg Ser
    1160                1165                1170

His Leu Ala Gly Ile Ala Glu Ala Ser His His Met Glu Tyr Ile
    1175                1180                1185

Ser Asp Ser Glu Lys Leu Thr Phe Pro Leu Ile Met Gly Thr Val
    1190                1195                1200

Gly Arg Ala Leu Phe Val Ser Leu Tyr Ser Ser Gln Gln Lys Ile
    1205                1210                1215

Glu Lys Thr Leu Lys Ile Ala Tyr Thr Glu Tyr Leu Ser Ala Ile
    1220                1225                1230

Asn Phe His Glu Arg Asn Ile Asp Asp Ala Asp Lys Thr Trp Val
    1235                1240                1245

His Asn Ile Glu Phe Val Glu Ala Met Cys His Asp Asn Tyr Thr
    1250                1255                1260

Thr Ser Gly Ser Ile Ala Phe Gln Arg Arg Thr Arg Asn Asn Ile
    1265                1270                1275

Leu Arg Phe Ala Thr Ile Pro Asn Ala Ile Leu Leu Asp Ser Met
    1280                1285                1290

Arg Met Ile Tyr Lys Lys Trp His Thr Tyr Thr His Ser Lys Ser
    1295                1300                1305

Leu Glu Lys Gln Glu Arg Asn Asp Phe Arg Asn Phe Ala Gly Ile
    1310                1315                1320

Leu Ala Ser Leu Ser Gly Ile Leu Phe Ile Asn Lys Lys Ile Leu
    1325                1330                1335

Gln Glu Met Tyr Pro Tyr Leu Leu Asp Thr Val Ser Glu Leu Lys
    1340                1345                1350

Lys Asn Ile Asp Ser Phe Ile Ser Lys Gln Cys Gln Trp Leu Asn
    1355                1360                1365

Tyr Pro Asp Leu Leu Thr Arg Glu Asn Ser Arg Asp Ile Leu Ser
    1370                1375                1380

Val Glu Leu His Pro Leu Ser Phe Asn Leu Leu Phe Asn Asn Leu
    1385                1390                1395

Arg Leu Lys Leu Lys Glu Leu Ala Cys Ser Asp Leu Ser Ile Pro
    1400                1405                1410

Glu Asn Glu Ser Ser Tyr Val Leu Leu Glu Gln Ile Ile Lys Met
    1415                1420                1425

Leu Arg Thr Ile Leu Gly Arg Asp Asp Asp Asn Tyr Val Met Met
    1430                1435                1440

Leu Phe Ser Thr Glu Ile Val Asp Leu Ile Asp Leu Leu Thr Asp
    1445                1450                1455

Glu Ile Lys Lys Ile Pro Ala Tyr Cys Pro Lys Tyr Leu Lys Ala
    1460                1465                1470

Ile Ile Gln Met Thr Lys Met Phe Ser Ala Leu Gln His Ser Glu
    1475                1480                1485

Val Asn Leu Gly Val Lys Asn His Phe His Val Lys Asn Lys Trp
    1490                1495                1500

Leu Arg Gln Ile Thr Asp Trp Phe Gln Val Ser Ile Ala Arg Glu
    1505                1510                1515

Tyr Asp Phe Glu Asn Leu Ser Lys Pro Leu Lys Glu Met Asp Leu
    1520                1525                1530

Val Lys Arg Asp Met Asp Ile Leu Tyr Ile Asp Thr Ala Ile Glu
    1535                1540                1545
```

```
Ala Ser Thr Ala Ile Ala Tyr Leu Thr Arg His Thr Phe Leu Glu
    1550                1555                1560

Ile Pro Pro Ala Ala Ser Asp Pro Glu Leu Ser Arg Ser Arg Ser
    1565                1570                1575

Val Ile Phe Gly Phe Tyr Phe Asn Ile Leu Met Lys Gly Leu Glu
    1580                1585                1590

Lys Ser Ser Asp Arg Asp Asn Tyr Pro Val Phe Leu Arg His Lys
    1595                1600                1605

Met Ser Val Leu Asn Asp Asn Val Ile Leu Ser Leu Thr Asn Leu
    1610                1615                1620

Ser Asn Thr Asn Val Asp Ala Ser Leu Gln Phe Thr Leu Pro Met
    1625                1630                1635

Gly Tyr Ser Gly Asn Arg Asn Ile Arg Asn Ala Phe Leu Glu Val
    1640                1645                1650

Phe Ile Asn Ile Val Thr Asn Tyr Arg Thr Tyr Thr Ala Lys Thr
    1655                1660                1665

Asp Leu Gly Lys Leu Glu Ala Ala Asp Lys Phe Leu Arg Tyr Thr
    1670                1675                1680

Ile Glu His Pro Gln Leu Ser Ser Phe Gly Ala Ala Val Cys Pro
    1685                1690                1695

Ala Ser Asp Ile Asp Ala Tyr Ala Ala Gly Leu Ile Asn Ala Phe
    1700                1705                1710

Glu Thr Arg Asn Ala Thr His Ile Val Val Ala Gln Leu Ile Lys
    1715                1720                1725

Asn Glu Ile Glu Lys Ser Ser Arg Pro Thr Asp Ile Leu Arg Arg
    1730                1735                1740

Asn Ser Cys Ala Thr Arg Ser Leu Ser Met Leu Ala Arg Ser Lys
    1745                1750                1755

Gly Asn Glu Tyr Leu Ile Arg Thr Leu Gln Pro Leu Leu Lys Lys
    1760                1765                1770

Ile Ile Gln Asn Arg Asp Phe Phe Glu Ile Glu Lys Leu Lys Pro
    1775                1780                1785

Glu Asp Ser Asp Ala Glu Arg Gln Ile Glu Leu Phe Val Lys Tyr
    1790                1795                1800

Met Asn Glu Leu Leu Glu Ser Ile Ser Asn Ser Val Ser Tyr Phe
    1805                1810                1815

Pro Pro Pro Leu Phe Tyr Ile Cys Gln Asn Ile Tyr Lys Val Ala
    1820                1825                1830

Cys Glu Lys Phe Pro Asp His Ala Ile Ile Ala Ala Gly Ser Phe
    1835                1840                1845

Val Phe Leu Arg Phe Phe Cys Pro Ala Leu Val Ser Pro Asp Ser
    1850                1855                1860

Glu Asn Ile Ile Asp Ile Ser His Leu Ser Glu Lys Arg Thr Phe
    1865                1870                1875

Ile Ser Leu Ala Lys Val Ile Gln Asn Ile Ala Asn Gly Ser Glu
    1880                1885                1890

Asn Phe Ser Arg Trp Pro Ala Leu Cys Ser Gln Lys Asp Phe Leu
    1895                1900                1905

Lys Glu Cys Ser Asp Arg Ile Phe Arg Phe Leu Ala Glu Leu Cys
    1910                1915                1920

Arg Thr Asp Arg Thr Ile Asp Ile Gln Val Arg Thr Asp Pro Thr
    1925                1930                1935
```

```
Pro Ile Ala Phe Asp Tyr Gln Phe Leu His Ser Phe Val Tyr Leu
    1940                1945                1950

Tyr Gly Leu Glu Val Arg Arg Asn Val Leu Asn Glu Ala Lys His
    1955                1960                1965

Asp Asp Gly Asp Ile Asp Gly Asp Asp Phe Tyr Lys Thr Thr Phe
    1970                1975                1980

Leu Leu Ile Asp Asp Val Leu Gly Gln Leu Gly Gln Pro Lys Met
    1985                1990                1995

Glu Phe Ser Asn Glu Ile Pro Ile Tyr Ile Arg Glu His Met Asp
    2000                2005                2010

Asp Tyr Pro Glu Leu Tyr Glu Phe Met Asn Arg His Ala Phe Arg
    2015                2020                2025

Asn Ile Glu Thr Ser Thr Ala Tyr Ser Pro Ser Val His Glu Ser
    2030                2035                2040

Thr Ser Ser Glu Gly Ile Pro Ile Ile Thr Leu Thr Met Ser Asn
    2045                2050                2055

Phe Ser Asp Arg His Val Asp Ile Asp Thr Val Ala Tyr Lys Phe
    2060                2065                2070

Leu Gln Ile Tyr Ala Arg Ile Trp Thr Thr Lys His Cys Leu Ile
    2075                2080                2085

Ile Asp Cys Thr Glu Phe Asp Glu Gly Gly Leu Asp Met Arg Lys
    2090                2095                2100

Phe Ile Ser Leu Val Met Gly Leu Leu Pro Glu Val Ala Pro Lys
    2105                2110                2115

Asn Cys Ile Gly Cys Tyr Tyr Phe Asn Val Asn Glu Thr Phe Met
    2120                2125                2130

Asp Asn Tyr Gly Lys Cys Leu Asp Lys Asp Asn Val Tyr Val Ser
    2135                2140                2145

Ser Lys Ile Pro His Tyr Phe Ile Asn Ser Asn Ser Asp Glu Gly
    2150                2155                2160

Leu Met Lys Ser Val Gly Ile Thr Gly Gln Gly Leu Lys Val Leu
    2165                2170                2175

Gln Asp Ile Arg Val Ser Leu His Asp Ile Thr Leu Tyr Asp Glu
    2180                2185                2190

Lys Arg Asn Arg Phe Thr Pro Val Ser Leu Lys Ile Gly Asp Ile
    2195                2200                2205

Tyr Phe Gln Val Leu His Glu Thr Pro Arg Gln Tyr Lys Ile Arg
    2210                2215                2220

Asp Met Gly Thr Leu Phe Asp Val Lys Phe Asn Asp Val Tyr Glu
    2225                2230                2235

Ile Ser Arg Ile Phe Glu Val His Val Ser Ser Ile Thr Gly Val
    2240                2245                2250

Ala Ala Glu Phe Thr Val Thr Phe Gln Asp Glu Arg Arg Leu Ile
    2255                2260                2265

Phe Ser Ser Pro Lys Tyr Leu Glu Ile Val Lys Met Phe Tyr Tyr
    2270                2275                2280

Ala Gln Ile Arg Leu Glu Ser Glu Tyr Glu Met Asp Asn Asn Ser
    2285                2290                2295

Ser Thr Ser Ser Pro Asn Ser Asn Asn Lys Asp Lys Gln Gln Lys
    2300                2305                2310

Glu Arg Thr Lys Leu Leu Cys His Leu Leu Leu Val Ser Leu Ile
    2315                2320                2325
```

```
Gly Leu Phe Asp Glu Ser Lys Lys Met Lys Asn Ser Ser Tyr Asn
2330                 2335                 2340

Leu Ile Ala Ala Thr Glu Ala Ser Phe Gly Leu Asn Phe Gly Ser
2345                 2350                 2355

His Phe His Arg Ser Pro Glu Val Tyr Val Pro Glu Asp Thr Thr
2360                 2365                 2370

Thr Phe Leu Gly Val Ile Gly Lys Ser Leu Ala Glu Ser Asn Pro
2375                 2380                 2385

Glu Leu Thr Ala Tyr Met Phe Ile Tyr Val Leu Glu Ala Leu Lys
2390                 2395                 2400

Asn Asn Val Ile Pro His Val Tyr Ile Pro His Thr Ile Cys Gly
2405                 2410                 2415

Leu Ser Tyr Trp Ile Pro Asn Leu Tyr Gln His Val Tyr Leu Ala
2420                 2425                 2430

Asp Asp Glu Glu Gly Pro Glu Asn Ile Ser His Ile Phe Arg Ile
2435                 2440                 2445

Leu Ile Arg Leu Ser Val Arg Glu Thr Asp Phe Lys Ala Val Tyr
2450                 2455                 2460

Met Gln Tyr Val Trp Leu Leu Leu Asp Asp Gly Arg Leu Thr
2465                 2470                 2475

Asp Ile Ile Val Asp Glu Val Ile Asn His Ala Leu Glu Arg Asp
2480                 2485                 2490

Ser Glu Asn Arg Asp Trp Lys Lys Thr Ile Ser Leu Leu Thr Val
2495                 2500                 2505

Leu Pro Thr Thr Glu Val Ala Asn Asn Ile Ile Gln Lys Ile Leu
2510                 2515                 2520

Ala Lys Ile Arg Ser Phe Leu Pro Ser Leu Lys Leu Glu Ala Met
2525                 2530                 2535

Thr Gln Ser Trp Ser Glu Leu Thr Ile Leu Val Lys Ile Ser Ile
2540                 2545                 2550

His Val Phe Phe Glu Thr Ser Leu Leu Val Gln Met Tyr Leu Pro
2555                 2560                 2565

Glu Ile Leu Phe Ile Val Ser Leu Leu Ile Asp Val Gly Pro Arg
2570                 2575                 2580

Glu Leu Arg Ser Ser Leu His Gln Leu Leu Met Asn Val Cys His
2585                 2590                 2595

Ser Leu Ala Ile Asn Ser Ala Leu Pro Gln Asp His Arg Asn Asn
2600                 2605                 2610

Leu Asp Glu Ile Ser Asp Ile Phe Ala His Gln Lys Val Lys Phe
2615                 2620                 2625

Met Phe Gly Phe Ser Glu Asp Lys Gly Arg Ile Leu Gln Ile Phe
2630                 2635                 2640

Ser Ala Ser Ser Phe Ala Ser Lys Phe Asn Ile Leu Asp Phe Phe
2645                 2650                 2655

Ile Asn Asn Ile Leu Leu Leu Met Glu Tyr Ser Ser Thr Tyr Glu
2660                 2665                 2670

Ala Asn Val Trp Lys Thr Arg Tyr Lys Lys Tyr Val Leu Glu Ser
2675                 2680                 2685

Val Phe Thr Ser Asn Ser Phe Leu Ser Ala Arg Ser Ile Met Ile
2690                 2695                 2700

Val Gly Ile Met Gly Lys Ser Tyr Ile Thr Glu Gly Leu Cys Lys
2705                 2710                 2715
```

Ala Met Leu Ile Glu Thr Met Lys Val Ile Ala Glu Pro Lys Ile
2720                2725                2730

Thr Asp Glu His Leu Phe Leu Ala Ile Ser His Ile Phe Thr Tyr
2735                2740                2745

Ser Lys Ile Val Glu Gly Leu Asp Pro Asn Leu Asp Leu Met Lys
2750                2755                2760

His Leu Phe Trp Phe Ser Thr Leu Phe Leu Glu Ser Arg His Pro
2765                2770                2775

Ile Ile Phe Glu Gly Ala Leu Leu Phe Val Ser Asn Cys Ile Arg
2780                2785                2790

Arg Leu Tyr Met Ala Gln Phe Glu Asn Glu Ser Glu Thr Ser Leu
2795                2800                2805

Ile Ser Thr Leu Leu Lys Gly Arg Lys Phe Ala His Thr Phe Leu
2810                2815                2820

Ser Lys Ile Glu Asn Leu Ser Gly Ile Val Trp Asn Glu Asp Asn
2825                2830                2835

Phe Thr His Ile Leu Ile Phe Ile Ile Asn Lys Gly Leu Ser Asn
2840                2845                2850

Pro Phe Ile Lys Ser Thr Ala Phe Asp Phe Leu Lys Met Met Phe
2855                2860                2865

Arg Asn Ser Tyr Phe Glu His Gln Ile Asn Gln Lys Ser Asp His
2870                2875                2880

Tyr Leu Cys Tyr Met Phe Leu Leu Tyr Phe Val Leu Asn Cys Asn
2885                2890                2895

Gln Phe Glu Glu Leu Leu Gly Asp Val Asp Phe Glu Gly Glu Met
2900                2905                2910

Val Asn Ile Glu Asn Lys Asn Thr Ile Pro Lys Ile Leu Leu Glu
2915                2920                2925

Trp Leu Ser Ser Asp Asn Glu Asn Ala Asn Ile Thr Leu Tyr Gln
2930                2935                2940

Gly Ala Ile Leu Phe Lys Cys Ser Val Thr Asp Glu Pro Ser Arg
2945                2950                2955

Phe Arg Phe Ala Leu Ile Ile Arg His Leu Leu Thr Lys Lys Pro
2960                2965                2970

Ile Cys Ala Leu Arg Phe Tyr Ser Val Ile Arg Asn Glu Ile Arg
2975                2980                2985

Lys Ile Ser Ala Phe Glu Gln Asn Ser Asp Cys Val Pro Leu Ala
2990                2995                3000

Phe Asp Ile Leu Asn Leu Leu Val Thr His Ser Glu Ser Asn Ser
3005                3010                3015

Leu Glu Lys Leu His Glu Glu Ser Ile Glu Arg Leu Thr Lys Arg
3020                3025                3030

Gly Leu Ser Ile Val Thr Ser Ser Gly Ile Phe Ala Lys Asn Ser
3035                3040                3045

Asp Met Met Ile Pro Leu Asp Val Lys Pro Glu Asp Ile Tyr Glu
3050                3055                3060

Arg Lys Arg Ile Met Thr Met Ile Leu Ser Arg Met Ser Cys Ser
3065                3070                3075

Ala

<210> SEQ ID NO 3
<211> LENGTH: 1278
<212> TYPE: DNA
<213> ORGANISM: Saccharomyces cerevisiae

```
<220> FEATURE:
<221> NAME/KEY: misc_feature
<223> OTHER INFORMATION: GRE3 coding sequence

<400> SEQUENCE: 3
cttctagggg gcctatcaag taaattactc ctggtacact gaagtatata agggatatag      60
aagcaaatag ttgtcagtgc aatccttcaa gacgattggg aaaatactgt aatataaatc     120
gtaaaggaaa attggaaatt ttttaaagat gtcttcactg gttactctta ataacggtct     180
gaaaatgccc ctagtcggct tagggtgctg gaaaattgac aaaaaagtct gtgcgaatca     240
aatttatgaa gctatcaaat taggctaccg tttattcgat ggtgcttgcg actacggcaa     300
cgaaaaggaa gttggtgaag gtatcaggaa agccatctcc gaaggtcttg tttctagaaa     360
ggatatattt gttgtttcaa agttatggaa caatttttcac catcctgatc atgtaaaatt     420
agctttaaag aagaccttaa gcgatatggg acttgattat ttagacctgt attatattca     480
cttcccaatc gccttcaaat atgttccatt tgaagagaaa taccctccag gattctatac     540
gggcgcagat gacgagaaga aaggtcacat caccgaagca catgtaccaa tcatagatac     600
gtaccgggct ctggaagaat gtgttgatga aggcttgatt aagtctattg gtgtttccaa     660 cttttcaggga agcttgattc aagatttatt acgtggttgt agaatcaagc ccgtggcttt     720
gcaaattgaa caccatcctt atttgactca agaacaccta gttgagtttt gtaaattaca     780
cgatatccaa gtagttgctt actcctcctt cggtcctcaa tcattcattg agatggactt     840
acagttggca aaaaccacgc caactctgtt cgagaatgat gtaatcaaga aggtctcaca     900
aaaccatcca ggcagtacca cttcccaagt attgcttaga tgggcaactc agagaggcat     960
tgccgtcatt ccaaaatctt ccaagaagga aaggttactt ggcaacctag aaatcgaaaa    1020
aaagttcact ttaacggagc aagaattgaa ggatatttct gcactaaatg ccaacatcag    1080
atttaatgat ccatggacct ggttggatgg taaattcccc acttttgcct gatccagcca    1140
gtaaaatcca tactcaacga cgatatgaac aaatttccct cattccgatg ctgtatatgt    1200
gtataaattt ttacatgctc ttctgtttag acacagaaca gctttaaata aaatgttgga    1260 tatactttt ctgcctgt                                                   1278

<210> SEQ ID NO 4
<211> LENGTH: 327
<212> TYPE: PRT
<213> ORGANISM: Saccharomyces cerevisiae

<400> SEQUENCE: 4

Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95
```

```
Leu Ser Asp Met Gly Leu Asp Tyr Leu Asp Leu Tyr Tyr Ile His Phe
            100                 105                 110

Pro Ile Ala Phe Lys Tyr Val Pro Phe Glu Lys Tyr Pro Pro Gly
        115                 120                 125

Phe Tyr Thr Gly Ala Asp Asp Glu Lys Lys Gly His Ile Thr Glu Ala
        130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
        290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325

<210> SEQ ID NO 5
<211> LENGTH: 648
<212> TYPE: DNA
<213> ORGANISM: Saccharomyces cerevisiae
<220> FEATURE:
<221> NAME/KEY: misc_feature
<223> OTHER INFORMATION: ISU1 coding sequence

<400> SEQUENCE: 5
tcttaaatcc ataagaacat cccttcatat aacaattgaa taaggaaaac acaacacata      60
acacatattt aacctgatgc ttcctgttat aacgagattt gcaaggcctg ctctgatggc     120
catcagacct gtgaatgcca tgggggtttt gagagcgtcc agcataacga aaaggcttta     180
tcatcccaag gtcatagagc attatacaca tccaagaaac gtcggctcat tagataaaaa     240
attgcccaac gtcggcactg gtctagtggg tgcgccagcg tgcggtgatg tgatgaggtt     300
gcagatcaaa gtcaacgact ctactggcgt tattgaagat gtcaaattca aacttttgg     360 atgtggctcc gccattgcct cctcttcata tatgactgaa ttggtacagg ggatgacctt     420
ggacgatgcg gcaaaaatta agaacactga aattgctaag gagttgagct tgcccccagt     480
caagttgcat tgctctatgt tagcggaaga tgcgatcaag gcagctatta aggactacaa     540
atctaagaga aacactccaa ccatgttatc gtaatgaata agaagataac cgggacaaga     600
acaagatcaa accctcacta atcaacaagt tggacttaat ttgtgcaa                  648
```

<210> SEQ ID NO 6
<211> LENGTH: 165
<212> TYPE: PRT
<213> ORGANISM: Saccharomyces cerevisiae

<400> SEQUENCE: 6

Met Leu Pro Val Ile Thr Arg Phe Ala Arg Pro Ala Leu Met Ala Ile
1               5                   10                  15

Arg Pro Val Asn Ala Met Gly Val Leu Arg Ala Ser Ser Ile Thr Lys
            20                  25                  30

Arg Leu Tyr His Pro Lys Val Ile Glu His Tyr Thr His Pro Arg Asn
        35                  40                  45

Val Gly Ser Leu Asp Lys Lys Leu Pro Asn Val Gly Thr Gly Leu Val
    50                  55                  60

Gly Ala Pro Ala Cys Gly Asp Val Met Arg Leu Gln Ile Lys Val Asn
65                  70                  75                  80

Asp Ser Thr Gly Val Ile Glu Asp Val Lys Phe Lys Thr Phe Gly Cys
                85                  90                  95

Gly Ser Ala Ile Ala Ser Ser Tyr Met Thr Glu Leu Val Gln Gly
            100                 105                 110

Met Thr Leu Asp Asp Ala Ala Lys Ile Lys Asn Thr Glu Ile Ala Lys
            115                 120                 125

Glu Leu Ser Leu Pro Pro Val Lys Leu His Cys Ser Met Leu Ala Glu
130                 135                 140

Asp Ala Ile Lys Ala Ala Ile Lys Asp Tyr Lys Ser Lys Arg Asn Thr
145                 150                 155                 160

Pro Thr Met Leu Ser
            165

<210> SEQ ID NO 7
<211> LENGTH: 729
<212> TYPE: DNA
<213> ORGANISM: Saccharomyces cerevisiae

<400> SEQUENCE: 7
atgctcctat ttccaagaag aactaatata gccttttca aaacaacagg catttttgct      60
aattttcctt tgctaggtag aaccattaca acttcaccat ctttccttac acataaactg    120
tcaaaggaag taaccagggc atcaacttcg cctccaagac caaagagaat tgttgtcgca    180
attactggtg cgactggtgt tgcactggga atcagacttc tacaagtgct aaaagagttg    240
agcgtagaaa cccatttggt gatttcaaaa tggggtgcag caacaatgaa atatgaaaca    300
gattgggaac cgcatgacgt ggcggccttg caaccaagac atactctgt cgtgatgtt    360 tctgcatgca tttcgtccgg atctttccag catgatggta tgattgttgt gccctgttcc    420
atgaaatcac tagctgctat tagaatcggt tttacagagg atttaattac aagagctgcc    480
gatgtttcga ttaaagagaa tcgtaagtta ctactggtta ctcgggaaac ccctttatct    540
tccatccatc ttgaaaacat gttgtcttta tgcagggcag tgttataat ttttcctccg      600 gtacctgcgt tttatacaag acccaagagc cttcatgacc tattagaaca agtgttggc    660 aggatcctag actgctttgg catccacgct gacactttc ctcgttggga aggaataaaa    720
agcaagtaa                                                             729

<210> SEQ ID NO 8
<211> LENGTH: 242
<212> TYPE: PRT
<213> ORGANISM: Saccharomyces cerevisiae

```
<400> SEQUENCE: 8

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
            20                  25                  30

Pro Ser Phe Leu Thr His Lys Leu Ser Lys Glu Val Thr Arg Ala Ser
        35                  40                  45

Thr Ser Pro Pro Arg Pro Lys Arg Ile Val Val Ala Ile Thr Gly Ala
    50                  55                  60

Thr Gly Val Ala Leu Gly Ile Arg Leu Leu Gln Val Leu Lys Glu Leu
65                  70                  75                  80

Ser Val Glu Thr His Leu Val Ile Ser Lys Trp Gly Ala Ala Thr Met
                85                  90                  95

Lys Tyr Glu Thr Asp Trp Glu Pro His Asp Val Ala Ala Leu Ala Thr
            100                 105                 110

Lys Thr Tyr Ser Val Arg Asp Val Ser Ala Cys Ile Ser Gly Ser
        115                 120                 125

Phe Gln His Asp Gly Met Ile Val Pro Cys Ser Met Lys Ser Leu
    130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Leu Val Thr Arg Glu
                165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
        195                 200                 205

Lys Ser Leu His Asp Leu Leu Glu Gln Ser Val Gly Arg Ile Leu Asp
    210                 215                 220

Cys Phe Gly Ile His Ala Asp Thr Phe Pro Arg Trp Glu Gly Ile Lys
225                 230                 235                 240

Ser Lys

<210> SEQ ID NO 9
<211> LENGTH: 1512
<212> TYPE: DNA
<213> ORGANISM: Saccharomyces cerevisiae

<400> SEQUENCE: 9
atgaggaagc taaatccagc tttagaattt agagacttta tccaggtctt aaaagatgaa      60
gatgacttaa tcgaaattac cgaagagatt gatccaaatc tcgaagtagg tgcaattatg    120
aggaaggcct atgaatccca cttaccagcc ccgttatta aaaatctcaa aggtgcttcg     180
aaggatcttt tcagcatttt aggttgccca gccggtttga agtaagga gaaaggagat      240 catggtagaa ttgcccatca tctggggctc gacccaaaaa caactatcaa ggaaatcata    300
gattatttgc tggagtgtaa ggagaaggaa cctctcccc caatcactgt tcctgtgtca     360
tctgcacctt gtaaaacaca tatctttct gaagaaaaaa tacatctaca agcctgcca      420 acaccatatc tacatgtttc agacggtggc aagtacttac aaacgtacgg aatgtggatt    480
cttcaaactc cagataaaaa atggactaat tggtcaattg ctagaggtat ggttgtagat    540
gacaagcata tcactggtct ggtaattaaa ccacaacata ttagacaaat tgctgactct    600
tgggcagcaa ttggaaaagc aaatgaaatt ccttcgcgt tatgttttgg cgttccccca     660
```

-continued

```
gcagctattt tagttagttc catgccaatt cctgaaggtg tttctgaatc ggattatgtt      720
ggcgcaatct tgggtgagtc ggttccagta gtaaaatgtg agaccaacga tttaatggtt      780
cctgcaacga gtgagatggt atttgagggt actttgtcct aacagatac acatctggaa       840 ggcccatttg gtgagatgca tggatatgtt ttcaaaagcc aaggtcatcc ttgtccattg      900
tacactgtca aggctatgag ttacagagac aatgctattc tacctgtttc gaaccccggt      960
ctttgtacgg atgagacaca taccttgatt ggttcactag tggctactga ggccaaggag     1020
ctggctattg aatctggctt gccaattctg gatgccttta tgccttatga ggctcaggct     1080
ctttggctta tcttaaaggt ggatttgaaa gggctgcaag cattgaagac aacgcctgaa     1140
gaattttgta agaaggtagg tgatatttac tttaggacaa aagttggttt tatagtccat     1200
gaaataattt tggtggcaga tgatatcgac atatttaact tcaaagaagt catctgggcc     1260
tacgttacaa gacatacacc tgttgcagat cagatggctt ttgatgatgt cacttctttt     1320
cctttggctc cctttgtttc gcagtcatcc agaagtaaga ctatgaaagg tggaaagtgc     1380
gttactaatt gcatatttag acagcaatat gagcgcagtt ttgactacat aacttgtaat     1440
tttgaaaagg gatatccaaa aggattagtt gacaaagtaa atgaaaattg gaaaaggtac     1500
ggatataaat aa                                                         1512
```

<210> SEQ ID NO 10
<211> LENGTH: 503
<212> TYPE: PRT
<213> ORGANISM: Saccharomyces cerevisiae

<400> SEQUENCE: 10

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220
```

-continued

```
Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
            245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
        290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
            325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
        370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
            485                 490                 495

Trp Lys Arg Tyr Gly Tyr Lys
            500
```

RECOMBINANT YEAST HAVING ENHANCED GAMMA VALEROLACTONE TOLERANCE AND METHODS OF USE

CROSS-REFERENCE TO RELATED APPLICATIONS

This application claims the benefit of U.S. Provisional Patent Application No. 62/048,458, filed Sep. 10, 2014; which is incorporated herein by reference as if set forth in its entirety.

STATEMENT REGARDING FEDERALLY SPONSORED RESEARCH OR DEVELOPMENT

This invention was made with government support under DE-FC02-07ER64494 awarded by the U.S. Department of Energy. The government has certain rights in the invention.

FIELD OF THE INVENTION

Broadly, the present invention relates to materials and methods for the production of ethanol. In particular, the present invention relates to genetically modified yeast strains useful for glucose and xylose fermentation and, more specifically, to strains of *Saccharomyces cerevisiae* genetically engineered for enhanced tolerance for gamma valerolactone (GVL) toxicity and methods of using the same for improved GVL-mediated hydrolysis of lignocellulosic biomass for industrial-scale ethanol production.

BACKGROUND

Cellulosic biomass is a vast source of renewable energy and an abundant substrate for biofuel production. As an alternative to corn-based ethanol, bioethanol can be generated from lignocellulosic (LC) sugars derived from cellulosic biomass of renewable and sustainable plant feedstocks. Energy of cellulosic biomass is primarily stored as the recalcitrant polysaccharide cellulose, which is difficult to hydrolyze because of the highly crystalline structure, and in hemicellulose, which presents challenges because of its structural diversity and complexity. Many microbes cannot natively ferment pentose sugars (e.g., xylose) from complex lignocellulosic biomass, which is composed of cellulose, hemicellulose and lignin fractions. Even when engineered to express the minimal enzymes from native pentose sugar-metabolizing organisms, *S. cerevisiae* cannot ferment xylose from innocuous lab media at industrially-acceptable rates. Laluce et al., *Applied Microbiol. Biotech.* 166:1908 (2012); Almeida et al., *Biotech. J.* 6:286 (2011). Xylose is a prevalent sugar in both woody and herbaceous plants and a major component of hemicelluloses. Bioconversion of both xylose and glucose is required for the production of cellulosic biofuels. To further complicate matters, plant biomass must be chemically, mechanically, or thermally pretreated prior to enzymatic hydrolysis ex situ in order to produce fermentable glucose and xylose monomers. Such pretreatment processes generate a diverse array of degradation products derived from plant cell walls, such as hemicellulose and lignin-derived acetate and aromatic molecules, many of which inhibit cellular metabolism in *S. cerevisiae* and induce microbial stress during hydrolysate fermentation. Taylor et al., *Biotechnology J.* 7:1169 (2012); Liu, *Applied Microbiol. Biotech.* 90:809 (2011). At present, little is known about how such inhibitors impact xylose fermentation, particularly under strict industrially relevant, anaerobic conditions where ethanol production is maximized.

In view of the current state of the biofuel industry, particularly ethanol production based on glucose- and xylose-containing feedstocks, it can be appreciated that there remains a need for efficient and cost-effective processes for breaking down cellulose and hemicellulose into their constituent sugars.

SUMMARY OF THE INVENTION

The present invention is largely related the inventors' research efforts to better understand xylose utilization for microbial engineering. The invention relates generally to methods and compositions for digesting lignocellulosic material and more particularly to methods that involve exposing the material to genetically engineered *Saccharomyces cerevisiae* (*S. cerevisiae*) variants having enhanced tolerance for or resistance to gamma valerolactone (GVL)-mediated toxicity.

In a first aspect, provided herein is a recombinant yeast that has been genetically engineered to exhibit a reduced amount of functional PAD1 polypeptide. The recombinant yeast has increased tolerance to gamma valerolactone (GVL) toxicity relative to a wild-type yeast or another recombinant yeast not exhibiting a reduced amount of functional PAD1 polypeptide. The recombinant yeast can further exhibit a reduced amount of functional FDC1 polypeptide, wherein the recombinant yeast has increased tolerance to gamma valerolactone (GVL) toxicity relative to a wild-type yeast or another recombinant yeast not exhibiting reduced amounts of functional PAD1 and FDC1 polypeptides. In some cases, a recombinant yeast comprises a disabling mutation in a gene encoding PAD1 polypeptide. The recombinant yeast can further comprise a disabling mutation in a gene encoding FDC1 polypeptide. The gene encoding PAD1 polypeptide can be SEQ ID NO:8. The gene encoding FDC1 polypeptide can be SEQ ID NO:10.

In some cases, a recombinant yeast further exhibits reduced or undetectable amounts of functional ISU1, GRE3, and IRA2 polypeptides, wherein the recombinant yeast is capable of increased aerobic or anaerobic xylose fermentation relative to a wild-type yeast or another recombinant yeast not exhibiting reduced amounts of functional PAD1, ISU1, GRE3, and IRA2 polypeptides. The recombinant yeast can have disabling mutation at each of loci isu1, gre3, and ira2, whereby the mutations result in reduced amounts of functional ISU1, GRE3, and IRA2 polypeptides, respectively. The disabling mutation at the gre3 locus can comprise a substitution of a threonine for the alanine at amino acid residue position 46 of SEQ ID NO:4. The disabling mutation at the ira2 locus can comprise a substitution of a stop codon for the glutamate at amino acid residue at position 2927 of SEQ ID NO:2. The disabling mutation at the isu1 locus can comprise a substitution of a tyrosine for the histidine at amino acid residue position 138 of SEQ ID NO:6. The recombinant yeast can produce ethanol at an increased rate relative to a wild-type yeast or another recombinant yeast not exhibiting reduced or undetectable amounts of functional ISU1, GRE3, and IRA2 polypeptides. The increased rate of ethanol production can occur under anaerobic conditions. The recombinant yeast can be of the genus *Saccharomyces*. The recombinant yeast can be of the species *Saccharomyces cerevisiae*. A portion of an extrachromosomal vector stably maintained in the recombinant yeast can comprise the disabling mutation. A nucleic acid sequence comprising the disabling mutation can be integrated into a chromosome of the recombinant yeast.

In another aspect, a yeast inoculum is provided herein. The yeast inoculum can comprise a recombinant yeast as described herein and a culture medium.

In a further aspect of the invention, a method for fermenting cellulosic material into ethanol is provided. The method comprises contacting a GVL-treated hydrosylate to a recombinant yeast or a yeast inoculum provided herein for a period of time sufficient to allow fermentation of at least a portion of the cellulosic material to ethanol, whereby the rate of fermentation of cellulosic material of the GVL-treated hydrosylate to ethanol is increased relative to the fermentation rate of a GVL-treated hydrosylate not contacted to the recombinant yeast or the yeast inoculum. The method can further comprise separating the ethanol from fermented cellulosic material. The GVL-treated hydrolysate can comprise xylose. The recombinant yeast can be *Saccharomyces cerevisiae*. The cellulosic material can comprise lignocellulosic biomass. In some cases, the lignocellulosic biomass comprises at least one material selected from the group consisting of agricultural residues, wood, municipal solid wastes, paper and pulp industry wastes, and herbaceous crops.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figures 1A, 1B:
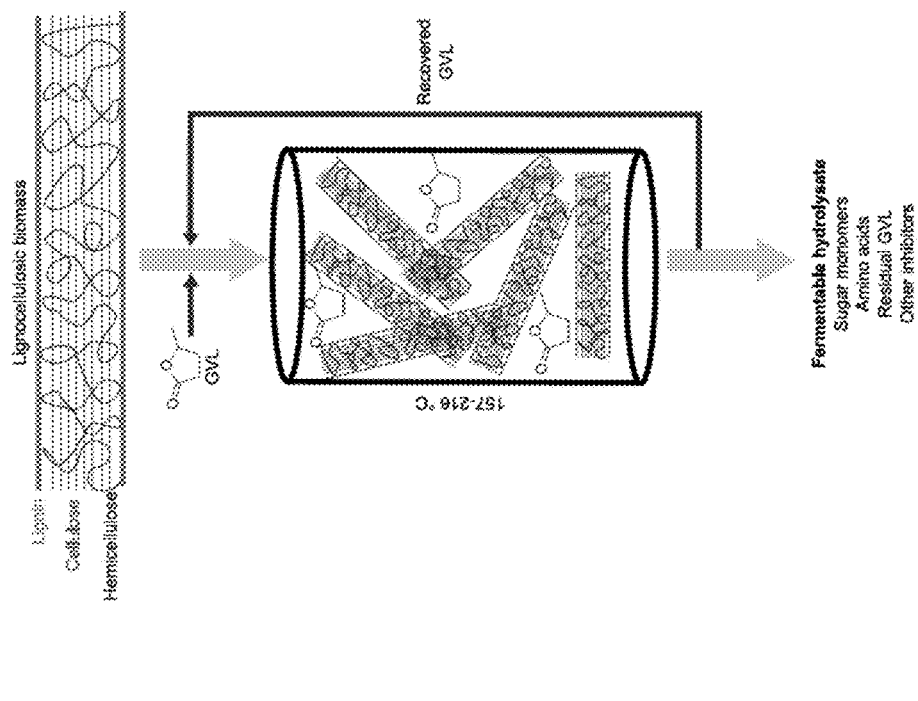
FIGS. 1A-1B show production of GVL hydrolysates and relative toxicity. Lignocellulosic biomass is heated with GVL to convert the cellulose and hemicellulose to sugar monomers, the result is a hydrolysate of sugars, amino acids, lignocellulosic derived fermentation inhibitors, and residual GVL that cannot be recovered (~1-3%) (A). The half-maximal inhibitory concentration ($IC_{50}$) of GVL in rich media is 2.7% (B).

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE INVENTION

In General

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The nucleotides which occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

As used herein, the term polynucleotide generally refers to any polyribonucleotide or polydeoxyribonucleotide, which may be unmodified RNA or DNA or modified RNA or DNA. Polynucleotides include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term polynucleotide also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including, for example, simple and complex cells. The term polynucleotide also embraces short polynucleotides often referred to as oligonucleotide(s).

The term "isolated nucleic acid" as used herein means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

Compositions of the Invention

Efficient biochemical conversion and fermentation of renewable lignocellulosic feedstocks is essential for the production of biofuels and other bioproducts from plant materials. While *S. cerevisiae* excel at fermentation of glucose from corn and sugar cane, the fermentation of renewable lignocellulosic biomass presents a significant challenge. Xylose, which is a pentose sugar and a major component of hemicellulose, can comprise almost 30% of total cell wall carbohydrate in grasses. Its conversion, along with glucose, into ethanol is critical for any economically-viable cellulosic biofuel process. Biomass pretreatments and enzymatic hydrolysis are viable but costly ways of depolymerizing cellulose and hemicellulose fractions of biomass to produce soluble carbohydrates. Large-scale depolymerization cellulose and hemicellulose fractions of biomass is increasingly economically feasible as the cost of pretreatment reagents drops. Acid-catalyzed hydrolysis methods are generally less expensive than enzyme-catalyzed methods. Gamma-valerolactone (GVL) is an inexpensive solvent that can be derived from cellulose or hemicelluloses. GVL promotes thermocatalytic saccharification through complete solubilization of all lignocellulosic biomass components including lignin, which makes GVL-mediated hydrolysis of lignocellulosic biomass a potentially transformative technology for biofuel production. Luterbacher et al., *Science* 343:277-280 (2014); see also Bond et al., *Integrated Catalytic Conversion of γ-Valerolactone to Liquid Alkenes for Transportation Fuels, Science* 26: (2010). Standard methods of GVL-mediated hydrosylation yields hydrolysates having high sugar levels (glucose and xylose) but also having residual levels of GVL that are toxic to fermentative microorganisms such as yeast. Current GVL-mediated hydrolysis methods yield hydrosylates comprising about 2.3% residual GVL. The present invention is based, at least in part, on the Inventors' discovery of genetic modifications that increase a yeast strain's tolerance for GVL toxicity and increase its growth rate in the presence of GVL.

Accordingly, one aspect of the present invention relates to eukaryotic host cells genetically engineered for improved tolerance to GVL toxicity. In particular, the present invention provides eukaryotic cells that have been genetically engineered to have enhanced GVL toxicity tolerance, enhanced anaerobic and/or aerobic xylose fermentation, and increased ethanol production relative to an unmodified cell or a recombinant cell not genetically engineered as described herein. Modified cells of the present invention are well-suited for producing a variety of fermentation products, including ethanol, in fermentation processes that use xylose or a combination of xylose and glucose as carbon sources.

As used herein, a "host cell" is a cell which has been transformed or transfected, or is capable of transformation or transfection by an exogenous polynucleotide sequence. A host cell that has been transformed or transfected may be more specifically referred to as a "recombinant host cell." A preferred host cell is a host cell that is naturally capable of alcoholic fermentation, preferably, anaerobic alcoholic fermentation. Host cells may also exhibit a high tolerance to ethanol, low pH, organic acids, and/or elevated temperatures. Such characteristics or activities of the host cell may be naturally present in the host cell or may be introduced or modified by genetic modification. Preferred host cells for the present invention include yeast cells, particularly yeast cells of the genus *Saccharomyces*. Preferred yeast species as host cells include *Saccharomyces cerevisiae, S. bulderi, S. barnetti, S. exiguus, S. uvarum, S. diastaticus, K. lactis, K. marxianus*, and *K. fragilis*, of which yeast cells of the genus *Saccharomyces* and yeast cells of the species *Saccharomyces cerevisiae* (*S. cerevisiae*) are preferred. Yeasts of the genus *Saccharomyces* posses both a metabolic pathway and a fermentative pathway for respiration.

"Yeasts" are eukaryotic micro-organisms classified in the kingdom Fungi. Most reproduce asexually by budding, although some yeasts undergo sexual reproduction by meiosis. Yeasts are unicellular, although some species with yeast forms may become multi-cellular through the formation of a string of connected budding cells known as pseudohyphae, or false hyphae, as seen in most molds. Yeasts do not form a single taxonomic or phylogenetic grouping. The term "yeast" is often taken as a synonym for *Saccharomyces cerevisiae*, but the phylogenetic diversity of yeasts is illustrated by their assignment to two taxonomic classes of fungi, the ascomycetes and the basidiomycetes.

In exemplary embodiments, a genetically modified yeast of the present invention comprises one or more genetic modifications that reduce or disrupt expression of functional PAD1 (phenylacrylic acid decarboxylase) polypeptide or functional FDC1 (ferulic acid decarboxylase) polypeptide. PAD1 and FDC1 are phenylacrylic acid decarboxylases that decarboxylate aromatic phenylacrylic acids (e.g., ferulic acid, p-coumaric acid, cinnamic acid) in *S. cerevisiae*. See Clausen et al., *Gene* 142(1):107-12 (1994); Mukai et al., *J. Bioscience & Bioengineering* 109(6):564-569 (2010). Full-length PAD1 (NCBI Gene ID: 852150) polypeptide is 242 amino acids. Full-length FDC1 (NCBI Gene ID: 852152) polypeptide is 503 amino acids. By "delete or disrupt", it is meant that the entire coding region of the gene is eliminated (deletion), or the gene or its promoter and/or terminator region is modified (such as by deletion, insertion, or mutation) such that the gene no longer produces a partially or fully non-functional polypeptide (i.e., lacking enzymatic activity), or produces an enzyme with severely reduced activity. The deletion or disruption can be accomplished by genetic engineering methods, forced evolution or mutagenesis, and/or selection or screening.

In some cases, a recombinant yeast of the present invention comprises a genetic modification that deletes or disrupts a Pad1 nucleic acid that encodes PAD1 polypeptide, whereby the genetically modified yeast produces a reduced level of functional PAD1 polypeptide. In some cases, such genetically modified yeast produce no or substantially no functional PAD1 polypeptide. In other embodiments, a recombinant yeast of the present invention comprises a genetic modification that deletes or disrupts a Fdc1 nucleic acid that encodes FDC1 polypeptide, whereby the genetically modified yeast produces a reduced level of functional FDC1 polypeptide. In some cases, such a genetically modified yeast produces no or substantially no functional PAD1 polypeptide. In some cases, it will be advantageous to genetically modify a host cell to comprise genetic modifications that cause reduced levels of both functional polypeptides, PAD1 and FDC1. Recombinant yeast comprising one or more of the genetic modifications described herein exhibit improve fermentation rates relative to unmodified yeast or yeast not comprising the genetic modifications described herein. Such recombinant yeast also exhibit increased tolerance to GVL toxicity and improved growth rates in hydrosylates comprising residual GVL following GVL-mediated hydrolysis.

It is contemplated that certain additional genetic modifications may be advantageous or necessary to produce other desirable characteristics and/or to enable the yeast cell to produce certain products at industrially-acceptable levels. For example, genetic modifications that reduce or eliminate functional PAD1 polypeptide or functional FDC1 polypeptide can be introduced into *S. cerevisiae* yeast of the GLBRCY133 ("Y133") strain (a GLBRCY128 derivative). Yeast of the GLBRCY128 ("Y128") strain were evolved for robust, anaerobic xylose metabolism under industrially relevant conditions and high yields of extracellular ethanol. Forced evolution of the Y128 yeast strain from a background strain designated NRRL YB-210/GLBRCY0 (Mortimer and Johnston, *Genetics* 113(1):35-43 (1986)), has been described elsewhere. See U.S. Application No. 61/978,585, filed Apr. 11, 2014. Yeast of the Y133 strain comprise the genotype of GLBRCY128, but with the loxP-KanMX-loxP marker excised by Cre as previously described (Parreiras et al., *PLoS One.* 2014; 9(9):e107499).

Accordingly, in some cases, a recombinant yeast of the present invention comprises a genetic modification that deletes or disrupts a Pad1 nucleic acid that encodes PAD1 polypeptide and further comprises a disabling mutation at each of loci isu1, gre3, and ira2, whereby the mutations result in reduced amounts of functional ISU1, GRE3, and IRA2 polypeptides.

The degree of GVL's toxicity to a microorganism such as yeast depends on the yeast's growth conditions. Generally, yeast grown in a minimal medium are more sensitive to chemical stress, while yeast grown in a nutrient-rich medium are more tolerant of chemical stress. Recombinant yeast of the present invention tolerate higher levels of GVL relative to a wild type yeast or yeast not comprising a genetic modification described herein when grown in either a nutrient-rich medium or minimal medium. In exemplary embodiments, a recombinant yeast of the present invention that comprises a genetic modification resulting in reduced levels of functional PAD1 polypeptide has significantly more GVL tolerance (P<0.05) than a yeast having the same genetic background but having normal levels of functional PAD1 polypeptide, even when growth under industrially relevant conditions in a minimal medium with high sugar loading (osmotically stressful). In general, toxicity is expressed as the "half maximal inhibitory concentration" or "$IC_{50}$." The terms "half maximal inhibitory concentration" and "$IC_{50}$" are used interchangeably and, as used herein, refer to a concentration of the compound that is required to inhibit a given biological or biochemical function by half. In a standard yeast lab strain, the $IC_{50}$ is about 1.98% GVL, while a PAD1 deletion mutant in the standard lab strain background has an $IC_{50}$ of about 2.4% GVL and FDC1 deletion mutant in the standard lab strain background has an $IC_{50}$ of about 2.1% GVL. In other words, a yeast having a genetic modification (in a standard lab strain background) that eliminates functional PAD1 polypeptide can tolerate GVL toxicity wherein GVL comprises about 2.4% of the hydrosylate. Similarly, yeast having a genetic modification (in a standard lab strain background) that eliminates functional FDC1 polypeptide can tolerate GVL toxicity wherein GVL comprises about 2.1% of the hydrosylate.

The GVL $IC_{50}$ for a genetically modified yeast of the present invention, when grown anaerobically in a minimal medium, is in the range between about 1.15% GVL and about 1.28% GVL, as compared to an $IC_{50}$ of about 1.0% for unmodified yeast of the xylose-fermenting background strain (Y128). When grown in a nutrient-rich media, yeast of the Y128 xylose-fermenting strain have an $IC_{50}$ of about 2.2% GVL, whereas genetically modified yeast of the present invention have an $IC_{50}$ of about 2.4% GVL to about 2.5% GVL. When grown in a nutrient-rich media, yeast of the Y133 xylose-fermenting strain have an $IC_{50}$ of about 2.7% GVL, whereas yeast of the genetically modified strain (e.g., Y133 pad1Δfdc1Δ) of the present invention has an $IC_{50}$ of about 2.9% GVL.

In some cases, a suitable host yeast cell comprises at least one native gene (a "xylose isomerase gene") that produces an active xylose isomerase enzyme that is capable of catalyzing the interconversion of D-xylose to D-xylulose. Xylose isomerase can also catalyze the interconversion of D-ribose to D-ribulose and D-glucose to D-fructose. The enzyme can be specific to the reduction of xylose or non-specific (i.e., capable of catalyzing the conversion of a range of pentose sugars). In some cases, a suitable host yeast cell is genetically engineered to contain an expression cassette containing *Clostridium phytofermentans* xylose isomerase (CphytoXylA), which can confer anaerobic xylose fermentation by *S. cerevisiae* with additional genetic modifications (see Brat et al., *Applied Environmental Microbiol.* 75:2304 (2009)), driven by the ScerTDH3 promoter. In exemplary embodiments, the expression cassette further comprises ScerTAL1, a Pentose Phosphate Pathway transaldolase enzyme that can improve xylose metabolism when overexpressed (see Ni et al., *Applied Environmental Microbiol.* 73:2061 (2007); Walfridsson et al., *Applied Environmental Microbiol.* 61:4184 (1995)), and SstipXYL3 driven by the ScerPGK1 and ScerTEF2 promoters, respectively. For example, the host yeast cell can comprise a TAL1-XylA-XYL3 gene expression cassette.

Genetic modification of the host cell can be accomplished in one or more steps via the design and construction of appropriate vectors and transformation of the host cell with those vectors. Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into the cloning vector, the vector transformed into a cloning host, e.g., *E. coli*, the cloning host grown up, lysed, the plasmid isolated and the fragment analyzed by restriction analysis, sequencing, combinations thereof, or the like.

Targeted integration can be accomplished by designing a vector having regions that are homologous to the upstream (5'-) and downstream (3'-) flanks of the target gene. Either of both of these regions may include a portion of the coding region of the target gene. The gene cassette (including associated promoters and terminators if different from those of the target gene) and selection markers (with associated promoters and terminators as may be needed) can reside on a vector between the regions that are homologous to the upstream and downstream flanks of the target gene. Targeted cassette insertion can be verified by any appropriate method such as, for example, PCR. A host cell may be transformed according to conventional methods that are known to practitioners in the art. Electroporation and/or chemical (such as calcium chloride- or lithium acetate-based) transformation methods can be used. The DNA used in the transformations can either be cut with particular restriction enzymes or used as circular DNA. Methods for transforming yeast strains are described in WO 99/14335, WO 00/71738, WO 02/42471, WO 03/102201, WO 03/102152 and WO 03/049525; these methods are generally applicable for transforming host cells in accordance with this invention. Other methods for transforming eukaryotic host cells are well known in the art such as from standard handbooks, such as Sambrook and Russel (2001) "Molecular Cloning: A Laboratory Manual (3rd edition)," Cold Spring Harbor Laboratory, Cold Spring Harbor Laboratory Press, or F. Ausubel et al., eds., "Current protocols in molecular biology," Green Publishing and Wiley Interscience, New York (1987).

In another aspect, compositions of the present invention further include yeast inocula comprising recombinant yeast as provided herein. A yeast inoculum of the present invention comprises (a) a recombinant yeast as provided herein and (b) a culture medium. In exemplary embodiments, the recombinant yeast is *S. cerevisiae* and the culture medium is a liquid culture medium. Yeast inocula of the present invention include large-scale preparations of sufficient quantities of viable yeast cells for use in, for example, xylose fermentation and other industrial ethanol-producing methods. When contacted to a GVL-treated hydrosylate comprising some level of residual GVL, a yeast inoculum of the present invention exhibits improved xylose fermentation rates and increased growth rates relative to a yeast inoculum that does not comprises a recombinant yeast of the present invention.

Methods of the Invention

The methods provided by the present invention involve the discovery and incorporation of genetic modifications into genes encoding certain polypeptides into a single host organism and the use of those organisms to convert xylose to ethanol. In particular, the present invention provides a method of fermenting cellulosic material comprising the 5-carbon sugar xylose into ethanol, where the method comprises use of a recombinant yeast having enhanced tolerance of GVL relative to wild type yeast or a recombinant yeast not comprising the genetic modifications described herein.

In exemplary embodiments, recombinant yeast of the present invention are used to make ethanol by converting xylose and other sugars under appropriate fermentation conditions. The sugars can come from a variety of sources including, but not limited to, cellulosic material. The cellulosic material can be lignocellulosic biomass. As used herein, the term "lignocellulosic biomass" refers to any materials comprising cellulose, hemicellulose, and lignin, wherein the carbohydrate polymers (cellulose and hemicelluloses) are tightly bound to the lignin. Generally, lignocellulosic material for making ethanol is feedstock such as corn stover, which consists of the stems, cobs, and leaves from the corn plants (i.e., the non-grain material). Corn stover is typically shredded by mechanical means and incorporated by tillage into topsoil for decomposition. In addition to lignocellulosic ethanol production from corn stover, other feedstocks such as sorghum, wheat, or another grain can be used. In some cases, lignocellulosic biomass comprises material selected from the group consisting of materials that comprise at least 75% cellulose, cellulose/hemicelluloses, xylose, biomass, and chitin. In other cases, the lignocellulosic biomass comprises at least one material selected from the group consisting of agricultural residues, wood, municipal solid wastes, paper and pulp industry wastes, and herbaceous crops. As used herein, the term "biomass" refers to a renewable energy source, is biological material from living or recently living organisms. As an energy source, biomass can either be used directly, or converted into other energy products such as biofuel. Biomass includes plant or animal matter that can be converted into fibers or other industrial chemicals, including biofuels. Industrial biomass can be grown from numerous types of plants, including miscanthus, switchgrass, hemp, corn, poplar, willow, sorghum, sugarcane, bamboo, and a variety of tree species, ranging from eucalyptus to oil palm (palm oil). Thus, biomass can include wood biomass and non-wood biomass.

In some cases, methods of the present invention include a hydrolyzation step. For example, when cellulosic material is used in the methods disclosed herein, the material can be hydrolyzed to produce a hydrolysate comprising xylose and glucose, which is subsequently contacted to one or more recombinant yeasts of the present invention. As used herein, the term "hydrolysate" refers to a fermentable sugar-containing product produced from cellulosic material (e.g., biomass), typically through pretreatment and saccharification processes. In exemplary embodiments, cellulosic material is pretreated using a solvent comprising gamma-valerolactone (GVL or γ-valerolactone). Such a pretreatment may also comprise one or more physical or chemical treatments such as grinding, milling, cutting, base treatment such as with ammonia or NaOH, and acid treatment.

In some cases, GVL-mediated hydrolysis further comprises an enzymatic saccharification treatment. Enzymatic saccharification typically makes use of an enzyme composition or blend to break down cellulose and/or hemicellulose and to produce a GVL-treated hydrolysate containing 6-carbon sugars (e.g., glucose) and 5-carbon sugars (e.g., xylose, arabinose) For review of saccharification enzymes, see Lynd et al., *Microbiol. Mol. Biol. Rev.* 66:506-577 (2002). Saccharification enzymes may be obtained commercially. In some cases, saccharification enzymes may be produced using recombinant microorganisms that have been engineered to express one or more saccharifying enzymes.

Following hydrolyzation, a GVL-treated hydrosylate is contacted with one or more of the genetically engineered yeasts disclosed herein (e.g., a yeast strain genetically modified to exhibit reduced amounts of functional PAD1 polypeptide and/or functional FDC1 polypeptide) under conditions suitable for fermentation. Fermentation conditions can comprise aerobic or anaerobic conditions. In exemplary embodiments, a method of the invention comprises contacting under anaerobic conditions a recombinant yeast as provided herein to a GVL-treated hydrosylate for a period of time sufficient to allow fermentation of at least a portion of the cellulosic material into ethanol. In exemplary embodiments, a recombinant yeast used according to the methods provided herein is *Saccharomyces cerevisiae*. As used herein, "anaerobic fermentation" refers to a fermentation process run in the absence of oxygen or in which substantially no oxygen is consumed, preferably less than 5, 2.5, or 1 mmol/L/h, more preferably 0 mmol/L/h is consumed (i.e., oxygen consumption is not detectable), and where organic molecules serve as both electron donor and electron acceptors. In the absence of oxygen, NADH produced in glycolysis and biomass formation cannot be oxidized by oxidative phosphorylation.

In another aspect, the present invention provides a method of fermenting cellulosic material comprising the 5-carbon sugar xylose into ethanol, where the method comprises use of a recombinant yeast having enhanced tolerance of GVL relative to a wild type yeast or a recombinant yeast not comprising the genetic modifications described herein. In particular, the present invention provides a method whereby the rate of fermentation of cellulosic material in a GVL-treated hydrosylate to ethanol is increased relative to the fermentation rate of a GVL-treated hydrosylate not contacted to a recombinant yeast or yeast inoculum provided by the present invention. In such cases, the method comprises contacting a GVL-treated hydrosylate to a recombinant yeast having increased tolerance to GVL toxicity, whereby cellulosic material of the contacted hydrosylate is fermented to produce ethanol at an enhanced rate relative to fermentation of a GVL-treated hydrosylate that has not been contacted to a recombinant yeast of the present invention.

In some cases, methods of the present invention further comprise an ethanol separation or extraction step. Following conversion of sugars into ethanol, the ethanol can be separated from a fermentation culture using, for example, a standard distillation method or by filtration using membranes or membrane systems known in the art. Methods of separating or extracting are not restricted to those disclosed herein.

Methods of the present invention can be conducted continuously, batch-wise, or some combination thereof.

In some cases, a genetically engineered yeast disclosed herein can be used to produce ethanol from glycerol. Glycerol is a by-product of biodiesel production, which, using a recombinant yeast of the present invention, could be further converted to ethanol. In some cases, a method of converting glycerol to ethanol can comprise contacting glycerol to one or more of the genetically engineered yeasts disclosed herein (e.g., a yeast strain genetically modified to exhibit reduced amounts of functional PAD1 polypeptide and/or functional FDC1 polypeptide) under appropriate fermentation conditions. For example, a method of converting glycerol into ethanol can comprise contacting under anaerobic conditions a recombinant yeast as provided herein to glycerol for a period of time sufficient to allow fermentation of at least a portion of the glycerol into ethanol. In exemplary embodiments, a recombinant yeast used according to the methods provided herein is *Saccharomyces cerevisiae* (*S. cerevisiae*). In some cases, the glycerol is crude glycerol.

Following conversion of glycerol into ethanol, the ethanol can be separated from a fermentation culture using, for example, a standard distillation method or by filtration using membranes or membrane systems known in the art. Methods of separating or extracting are not restricted to those disclosed or exemplified herein.

Articles of Manufacture

In a further aspect, the present invention provides an article of manufacture containing any one or more of the recombinant yeasts disclosed herein is provided. An article of manufacture can contain one of the microorganisms disclosed herein (e.g., one or more of the yeast strains), or an article of manufacture can contain two or more of the microorganisms disclosed herein. Articles of manufacture disclosed herein also can include, for example, components necessary for growth of the particular microorganism(s).

While the present invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents and alternatives falling within the spirit and scope of the invention as defined by the appended claims.

The present invention will be more fully understood upon consideration of the following non-limiting Examples. All papers and patents disclosed herein are hereby incorporated by reference as if set forth in their entirety.

EXAMPLES

Genetic Engineering and Directed Evolution of a *S. cerevisiae* Strain Tolerant to GVL Toxicity Lignocellulosic biomass derived fuels and chemicals provide a suite sustainable bioproducts. Before biomass can be converted to fuel or compounds, it must be converted to fermentable sugars (pre-treatment and hydrolysis), and these sugars converted to fuels by microorganisms. Both pre-treatment and hydrolysis can imbue the resultant hydrolysates with toxicity arising from residual pre-treatment chemicals or biomass derived inhibitors [2, 3], which throttle fermentation rates at a substantial economic cost [4].

Fermentation inhibitors come in many forms, and the landscape of these inhibitors is constantly changing as new pre-treatment, hydrolysis, and feedstocks technologies are developed [2]. Enzymatic hydrolysis of biomass for fermentation releases small acids, phenolics, and furans that are a ubiquitous challenge to bioconversion [3, 5]. Chemical hydrolysis methods such as γ-valerolactone (GVL) and ionic liquids offer an enzyme free route to fermentable sugars, but come with their own challenges [6-8]. In addition to the small acid inhibitors, the chemicals used for hydrolysis can persist in residual amounts into the resultant hydrolysate, and these compounds are not biologically benign to fermentative microorganisms [7, 8]. Further, as these chemical catalyst are used in relatively large amounts during hydrolysis, they residual concentrations are often much higher than the small acid and phenolic inhibitors generated from the biomass.

GVL is a promising, new chemical hydrolysis technology to breakdown the cellulose polysaccharides to fermentable sugar monomers [6]. The advantage of GVL is that it is a recoverable and renewable chemical. One challenge of this method is the toxicity of residual GVL to fermentative microbes. GVL is mildly toxic to yeast, but this toxicity can be magnified when in combination with other inhibitors and the ethanol produced. As such, engineering GVL tolerant microbes is a means of overcoming toxicity, minimizing the costs of reagent recovery, and improving biofuels produced via ionic liquid hydrolysis.

We have used chemical genomics to discover the genome-wide response to toxicity. Using this information we have identified specific genes that mediate toxicity, and have engineered these specific mutations into an industrially viable, xylose-fermenting strain of *Saccharomyces cerevisiae*. This approach offer a rapid method of tailoring existing strains to specific chemical stressors found in industrial bioconversion.

GVL is the Major Inhibitor Found in GVL Hydrolysates:

GVL produced hydrolysates (FIG. 1A) are still largely unstudied, as such, our first goal was to identify the major inhibitors of GVL hydrolyates. LC/MS of hydrolysates revealed that three inhibitory compounds were highly abundant in the GVL hydrolysates: GVL, levulinic acid, and hydroxymethylfurfural (HMF); other lignocellulosic derived inhibitors were present, but at orders of magnitude lower concentrations (Table 1). GVL hydrolysates have a high level of residual GVL (230 mM), and as such this is the most toxic major inhibitor in GVL hydrolysates, given its half maximal inhibitory concentration ($IC_{50}$) is 270 mM (FIG. 1B). Because of this, we focused on understanding GVL toxicity and developing GVL-tolerant yeast strains.

TABLE 1

Quantification of the 10 most abundant fermentation inhibitors found in GVL hydrolysates

| Inhibitor | mM |
|---|---|
| GVL | 100-230 |
| Acetate | 30.27 |
| Formate | 25.12 |
| Levulinic acid | 17.13 |
| HMF | 10.80 |
| Acetaldehyde | 1.98 |
| Furfural | 1.33 |
| 2-ketoglutaric acid | 0.15 |
| Furoic Acid | 0.13 |
| Coumaric acid | 0.11 |

Figures 2A, 2B, 2C:
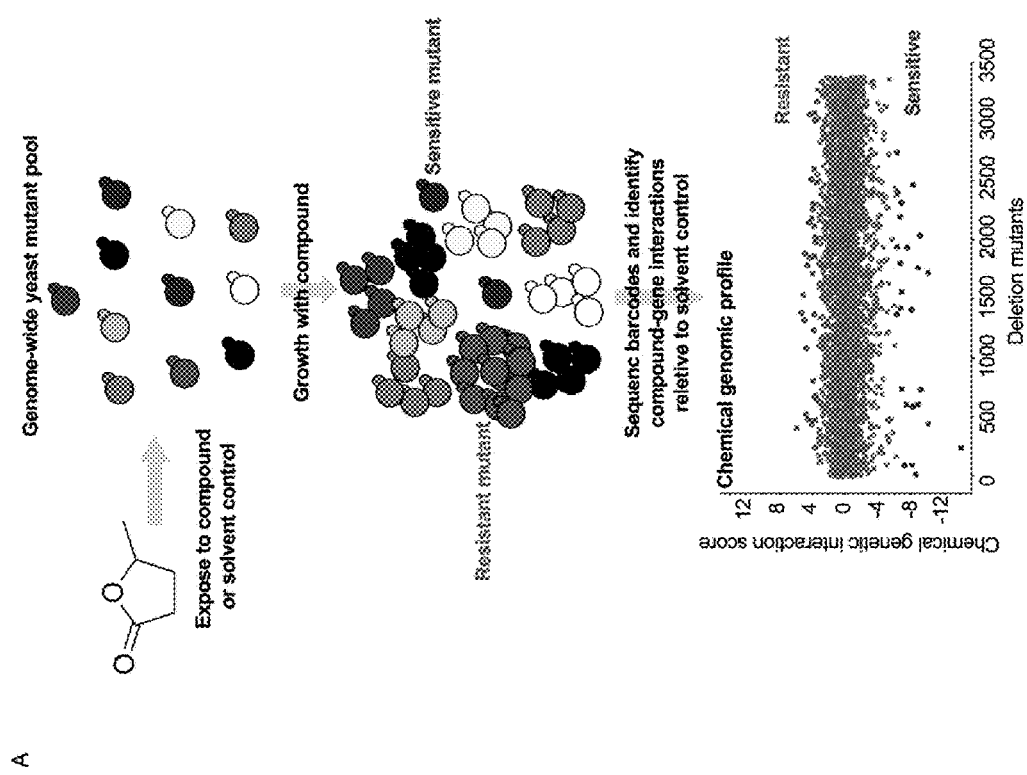
FIGS. 2A-2C show chemical genomic profiling of GVL. Chemical genomic profiling (A) revealed a significant enrichment for genes involved in late endosome to vacuole ($p<0.01$) among the top gene mutants sensitive to GVL (B). Single mutant validations of these individual mutants confirmed they were significantly more sensitive to GVL (C). (Mean±S.E., n=3).

Chemical Genomic Predicts GVL Targets Cellular Membranes and Membrane Bound Processes:

To understand the mode of action of GVL toxicity we conducted chemical genomic analysis (FIG. 2A). This is a reverse genetics method that uses collections of defined gene mutants, and uses the response of these mutants in the presence of a chemical stress to gain functional insight into the chemical's mode of action and cellular target. We first challenged the yeast deletion collection with media containing 230 mM GVL and used barcode sequencing to identify the fitness response of the individual deletion mutants.

Among the top 10 sensitive deletion mutants, we found significant enrichment for genes involved in late endosome to vacuole transport ($p<0.01$, FIG. 2B), driven by deletion mutants of SEC28, VPS38, DID2. We validated mutants within this GO terms using single mutants culture, and found all had a lower $IC_{50}$ compared to the control strain (FIG.

2C). Deletion mutants of these 3 genes have increased sensitivity to ethanol, heat, and membrane disrupting agents such as miconazole and nigercin. When we correlated the chemical genomic profile of GVL with the yeast genetic interaction network [10], we found significant enrichment for genes involved in golgi-vesicle mediated transport among the top 10 correlations (p=0.001). RET2 was consistently predicted as the top correlation for the GVL chemical genomic profile. Ret2p is a subunit of the coatomer complex involved in retrograde transport between Golgi and ER is also involved in golgi transport of vesicles [11]. RET2 mutants similarity show increased sensitivity to heat and membrane disrupting agents. We correlated the chemical genomic profile to GVL to existing chemical genomic datasets, and found its profile was significantly similar to profiles of nigericin (p<0.01) and papuamide (p<0.01), membrane destabilizing compounds. Taken together, these data suggest GVL could exert toxicity by damaging membrane integrity.

Figures 3A, 3B, 3C:
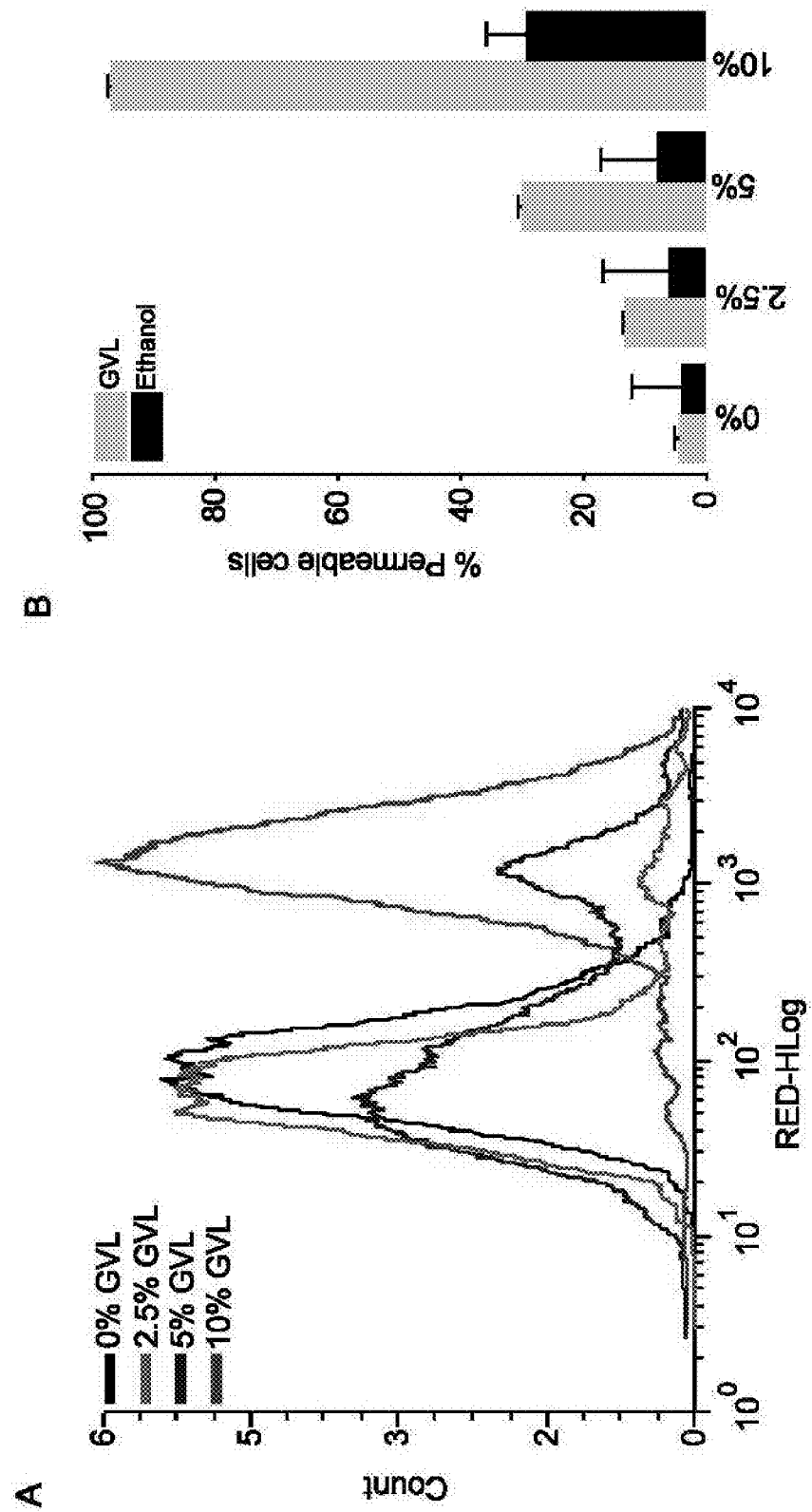
FIGS. 3A-3C demonstrate that GVL rapidly compromises membrane integrity and is synergistic with ethanol. GVL compromises membrane integrity as determined by dye uptake after treatment, and this effects is apparent with as little as 2.5% GVL (A, B). GVL is significantly synergistic with ethanol (C). (Mean±S.E, n=3).

GVL Damages Membranes and is Synergistic with Ethanol:

To confirm if GVL treatment can rapidly affect cell integrity, we assessed cell permeability after GVL treatment. Using FACS analysis combined with a dye that is only taken up by cells with damaged membranes, we found a rapid and dose dependent effect of GVL on leakage (FIGS. 3A, 3B), similar to the effects of ethanol but with a greater magnitude (FIG. 3B). Given that both GVL and ethanol can damage cellular membranes, we also tested if these compounds are synergistic. We found a strong synergism between GVL and ethanol in both our lab strain and xylose fermenting strain (FIG. 3C). At a 1% GVL concentration and 4% ethanol concentration, we saw a significant synergistic interaction between GVL and ethanol (p<0.01). This suggest that as ethanol titers increase during fermentation, the toxic effects of GVL and ethanol will magnify each other, which ultimately affects yield.

Figures 4A, 4B, 4C, 4D:
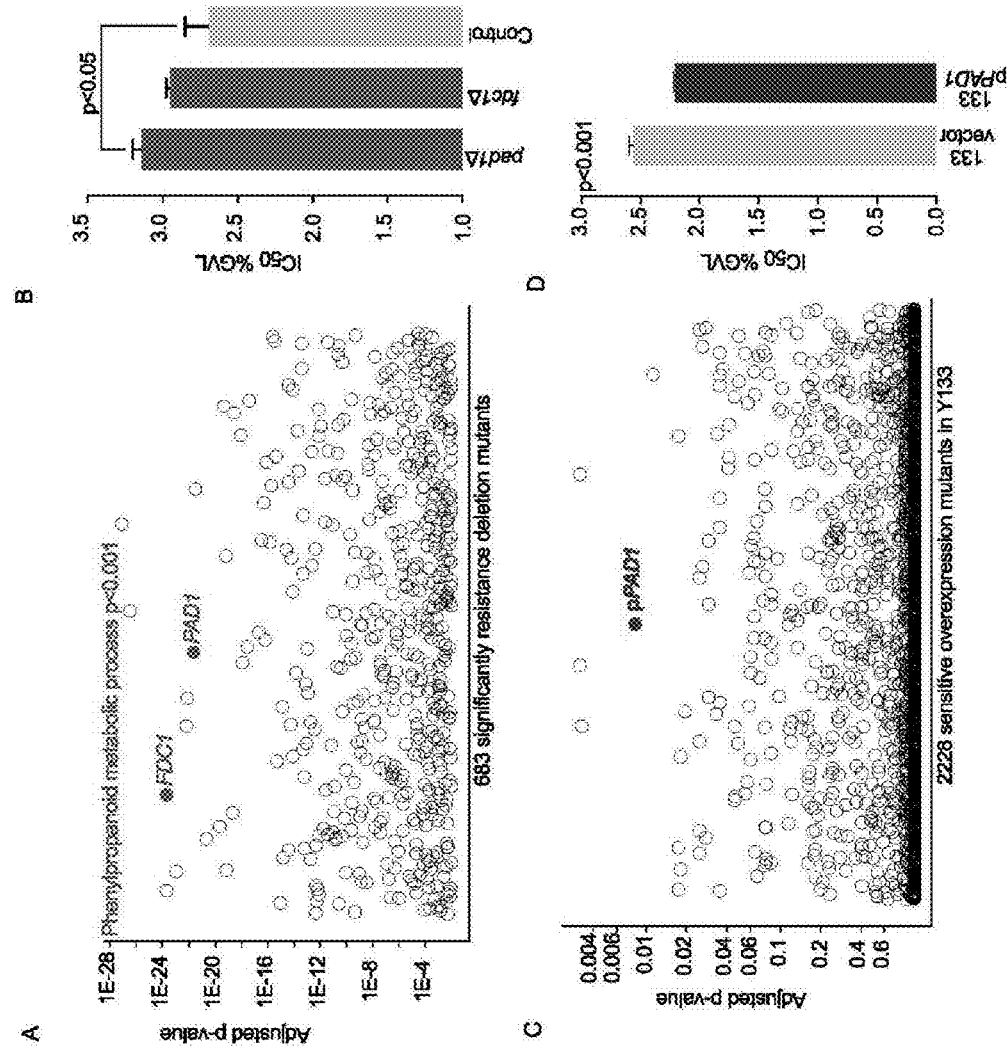
FIGS. 4A-4D present genes mediating GVL toxicity by deletion and overexpression mutant profiling. Among deletion mutants significantly resistant to GVL, we saw significant enrichment for genes in phenylpropanoid metabolism ($p<0.001$), driven by the mutants of the decarboxylases Pad1p and Fdc1p (A). Individual mutants in these genes were more tolerant of GVL (B). Overexpression profiling using MoBY-ORF transformed Y133 demonstrated that overexpression of PAD1 conferred significant GVL sensitivity (C). Increased expression of PAD1 significantly reduced GVL tolerance in single mutant cultures (D). (Mean±S.E, n=3).

Deletion of the Decarboxylases Pad1p and Fdc1p Enhance GVL Tolerance:

Importantly for our goal, we also looked for gene deletions that increased resistance to GVL. Among the top GVL resistance mutants we found a significant enrichment for genes involved in phenylpropanoid metabolic process (p<0.002, FIG. 4A), driven by deletion mutants of PAD1 and FDC1. Single mutant validations reveals deletion of these genes improved GVL tolerance (FIG. 4B). Pad1p is phenylacrylic acid decarboxylase with a reported role in aromatic acid catabolism and the ability to detoxify cinnamic acid [12, 13]. Like Pad1p, Fdc1p is thought to be a similar phenylacrylic acid decarboxylase involved in detoxifying ferulic acid [13].

Using chemical genomics guided biodesign, we identified 2 genes that are key in mediating GVL tolerance of the fermentative yeast S. cerevisiae. Deletion of the genes encoding acid decarboxylases Pad1 and Fdc1 conferred greater tolerance to GVL. These specific mutations were introduced into to an industrially viable, xylose fermenting yeast (GLBRCY-128) to create a ethanol producing yeast (GVL-R1) specifically tailored for GVL hydrolysates. Yeast of the GVL-R1 strain has the advantage of being able to grow and ferment both glucose and xylose faster than the GLBRC-Y128 strain in up to 2.5% residual GVL. Under our test conditions, GLBRC-Y128 required 72 hours to completely ferment all glucose, whereas engineered strain GVL-R1 achieved this in 48 hours. Importantly, engineered strain GVL-R1 was also able to ferment xylose, allowing for greater ethanol yields.

Overexpression Chemical Genomic Profiling Confirms Pad1p Mediates GVL Toxicity:

We wanted to extend our chemical genomic analysis to industrially an industrially relevant, xylose ferment yeast strain. Presently there are no available genome-wide deletion mutant collections in industrial yeast, so we took a complementary approach. The MoBY-ORF 2.0 plasmid collection is with barcoded versions of 95% of all S. cerevisiae genes each expressed on a 2µ plasmid [14]. This collection of plasmids can be pooled and transformed into any yeast to allow investigations of the effect of gene dose under stress conditions. We transformed a version of the xylose-fermenting yeast GLBRC-Y133 [15] en masse with the pooled plasmid collection and selected over 50K individual transformants (10× genome coverage). We grew this pooled transformant collection in the presence of 2.5% GVL or a water control under anaerobic conditions in glucose/xylose containing media and assessed the effects of increased gene dose on growth in the presence of GVL. We found the Pad1p overexpression mutant was one of the top sensitive strains (p<0.01, FIG. 4C). We confirmed with single mutant cultures that overexpression of PAD1 causes GVL sensitivity. The $IC_{50}$ of Y133$^+$ pPAD1 was 2.2%, compared to 2.56% of vector control (FIG. 4D, p<0.001).

Deletion of PAD1 and FDC1 in a Xylose Fermenting Strain Confers GVL Tolerance:

Chemical genomic profiling and validation of individual mutants confirmed that the decarboxylase Pad1p (and Fdc1p) were involved in GVL toxicity. We chose to engineer these deletions into a xylose fermenting yeast strain GLBRC Y133 (henceforth Y133). PAD1 and FDC1 are adjacent on chromosome IV, and as such we were able to delete both at the same time using transformation with PCR product of the antibiotic resistance marker KanMX flanked by homologous regions upstream of PAM and downstream of FDC1 (FIG. 4A). We confirmed deletion of both genes by PCR (FIG. 4B).

Figures 5A, 5B, 5C, 5D:
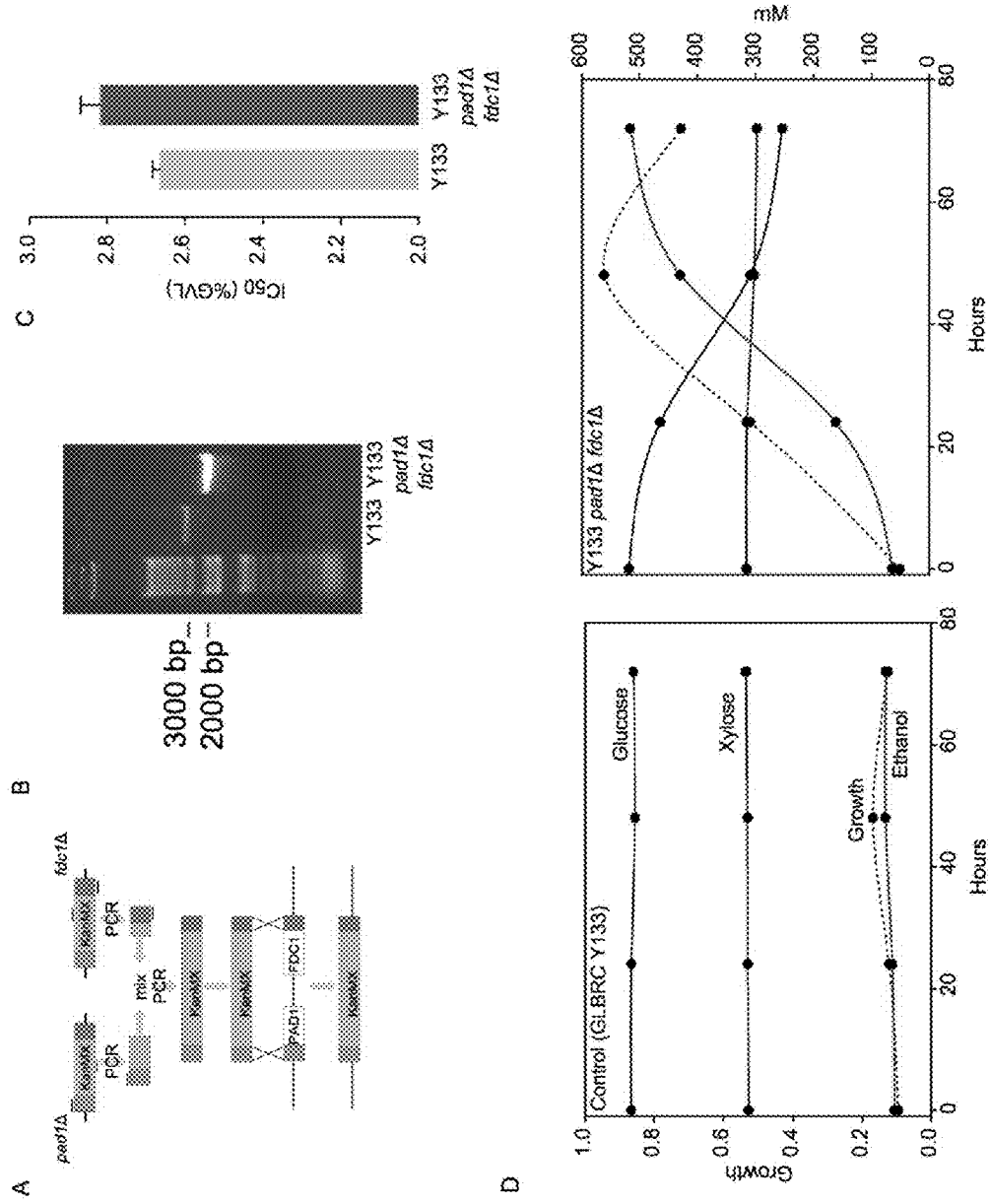
FIGS. 5A-5D demonstrate that deletion of PAD1 and FDC1 confers tolerance of GVL in a xylose fermenting yeast. A two-step PCR approach was used to simultaneously delete PAD1 and FDC1 in Y133, which are adjacent on chromosome IV (A), and confirmed deletion by PCR (B). The Y133 pad1Δfdc1Δ mutant had significantly greater ($p<0.01$) tolerance of GVL (C), and also had faster growth, sugar consumption, and ethanol production under anaerobic conditions in synthetic hydrolysate with 1% GVL (D).

The $IC_{50}$ concentration of GVL of the Y133 pad1Δfdc1Δ strain was significantly higher than the Y133 background (FIG. 5C; p<0.01). Finally, we tested the performance of the Y133 pad1Δfdc1Δ strain under industrially relevant anaerobic conditions in a synthetic hydrolysate containing 1% GVL. The double KO strain grew, consumed sugars, and produced ethanol, whereas the Y133 background strain did not (FIG. 5D).

Figures 6A, 6B, 6C, 6D:
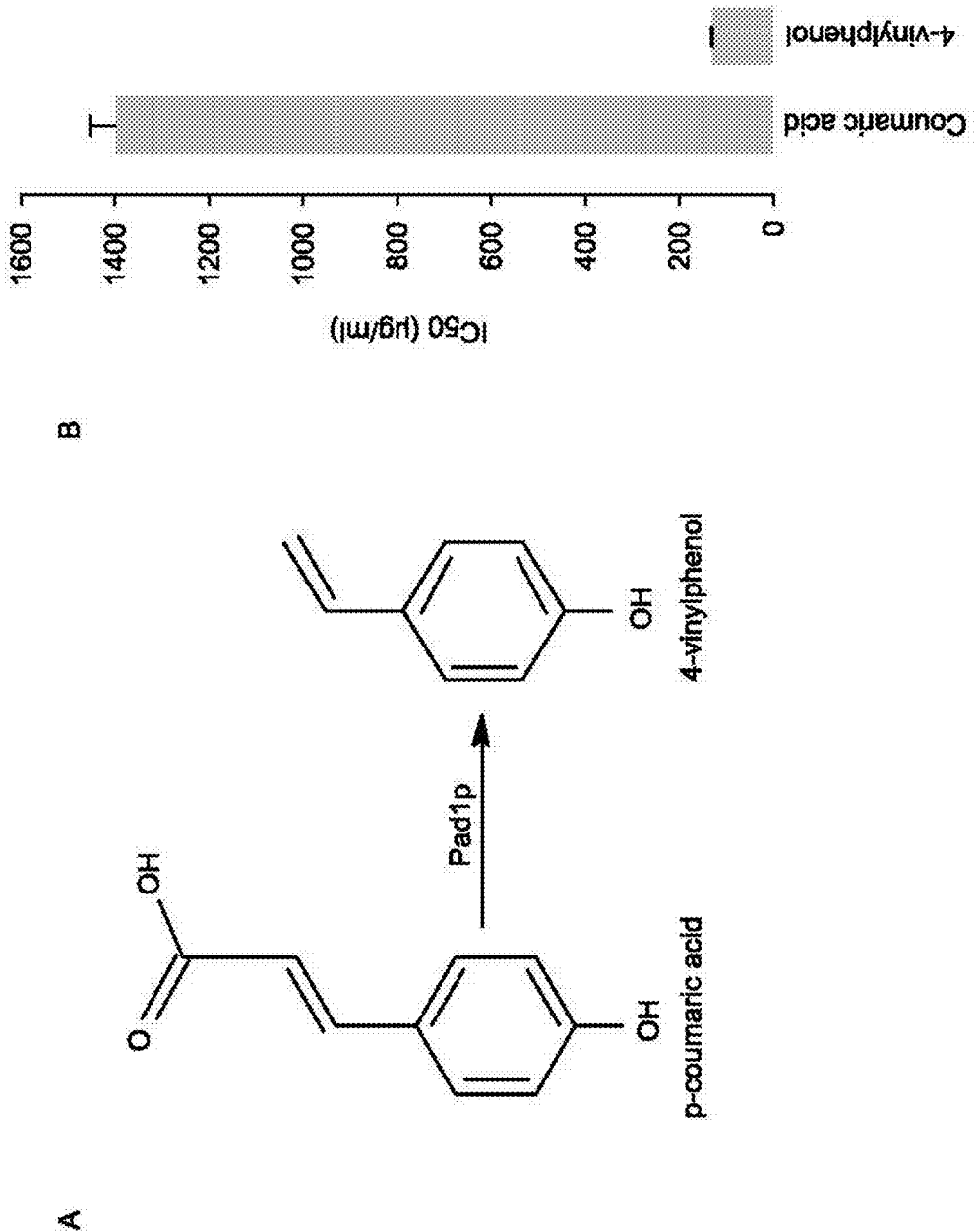
FIGS. 6A-6D demonstrate that vinyl products of PAD1 and FDC1 are more toxic than the acid precursors, and are synergistic with GVL. The decarboxylase Pad1p converts phenolic acids to a vinyl form (A). The vinyl derivative of coumaric acid (4-vinylphenol) is significantly more toxic than the acid form (B, $p<0.001$). 4-vinylphenol is significantly synergistic with GVL (C). Deletion of PAD1 and FDC1 confers resistance to coumaric acid (D).

Vinyl Products of Pad1p Decarboxylation are Synergistic with GVL:

PAD1 and FDC1 are known to convert phenolic acids into a vinyl form, and are thought to "detoxify" ferulic and coumaric acids; however, we posit that the vinyl derivatives (see FIG. 6A) may be more toxic than the acid forms. We found that the $IC_{50}$ values of the vinyl derivative of coumaric acid, 4-vinylphenol, was an order of magnitude lower than that of coumaric acid (FIG. 6B). Further, we found a statistically significant synergistic interaction between the vinyl derivative of coumaric acid, 4-vinylphenol, and GVL (FIG. 6C, p<0.01). Chemical genomic profiling of 4-vinylphenol revealed that, similar to GVL, RET2 was the top genetic interaction network correlation, and this compound was similarly predicted to target the membrane bound processes such as vesicle mediated transport. Deletion of PAD1 and FDC1 may reduce production of membrane damaging vinyls, which are synergistic with GVL. Our Y133 pad1Δfdc1Δ has a statistically significantly greater tolerance of coumaric acid (FIG. 6D, p<0.01), and we contend this is because less of the more toxic vinyl form is being generated.

Discussion

Through chemical genomic analysis we predicted and confirmed the chemical hydrolysis reagent gamma-valerolactone exerts toxicity by damaging cellular membranes, similar to ethanol and other membrane damaging drugs. Further, this compound is synergistic with ethanol. While this compound is less toxic than other fermentation inhibitors (e.g., furfural, HMF), the abundance of residual GVL in hydrolysates my ultimately limit ethanol production through a documented synergism with end-product fuels such as ethanol or isobutanol. The toxic effects of GVL can be alleviated by specific deletion of the cellular decarboxylases Pad1p and Fdc1p, which convert phenolic acids into a more toxic vinyl form that is synergistic with GVL. While these specific decarboxylases have been studied for their role in 'detoxifying' hydrolysates by converting phenolic acids, the vinyl products may ultimately have a greater effect on growth in phenolic rich hydrolysates.

The process technologies of lignocellulosic biofuel production are still evolving, and as a result the landscape of fermentation inhibitors is dynamic. Strain development is necessary to keep pace with these new chemical stressors. Industry relies on tried and true industrial yeast strains with favorable performance and may be hesitant to adopt new genetic backgrounds, no matter how well they are predicted to perform. We have used a functional genomics approach to identify points of rational engineering. As our discovery system is based on *Saccharomyces cerevisiae*, the primary bioethanol organism, these genes identified can be directly modified in other yeast strains to rapidly tailor proven strains to new purposes.

This approach can also be applied to other bioproducts. Through synthetic biology drugs, green chemicals, and next-generation fuels can be produced by yeast and other engineered microbes, and many of these end-products can be toxic to the producing biocatalyst. The genome-wide, functional view of their effects provided by chemical genomics could be useful in improving production. This system is not limited to yeast, genomic wide mutant and overexpression collections exist in a number of industrial relevant microbes, such as *E. coli* and *Zymomonas mobilis*, and as such, the same approach is translatable.

Methods

Compounds, Initial Screening, and $IC_{50}$ Determination:

Compounds tested were purchased from Sigma. Cells of *S. cerevisiae* (MATα pdr1Δ::natMX pdr3Δ::KI.URA3 snq2Δ::KI.LEU2 can1Δ::STE2pr-Sp_his5 lyp1Δ his3Δ1 leu2Δ0 ura3Δ0 met15Δ0), referred to as control strain, were grown in 200 μl cultures at 30° C. in YPD, with a drug or DMSO control. Plates were read on a TECAN M1000 over a 48 h growth period. The specific growth rate was calculated using GCAT analysis software (available at gcat3-pub.glbrc.org on the world wide web) [16]. When presented, $IC_{50}$ values for growth inhibition were calculated from triplicate 8 point dose curves and SigmaPlot 12.0. When presented, error bars are Mean±Standard error of at least 3 replicates.

Chemical Genomic Analysis:

Chemical genomic analysis of poacic acid was performed as described as described previously [17, 18]. The tested yeast deletion collection had ~4000 strains using the genetic background described in Andrusiak (2012) [19]. The optimal inhibitory concentration of poacic acid for chemical genomic profiling (70-80% growth versus solvent control in YP-galactose media after 24 hours of growth) was determined using an 8 point dose curve. A concentration of 88 μg/ml inhibited growth within this range. 200 μl cultures of the pooled, deletion collection of *S. cerevisiae* deletion mutants were grown with 88 μg/ml poacic acid or a DMSO control in triplicate for 48 h at 30° C. Genomic DNA was extracted using the Epicentre MasterPure™ Yeast DNA purification kit. Mutant-specific molecular barcodes were amplified with specially designed multiplex primers [20]. The barcodes were sequenced using an Illumina MiSeq. 3 replicates of each condition (poacic acid vs DMSO) were sequenced. One DMSO control was lost due to poor sequencing reads. The barcode counts for each yeast deletion mutant in the presence of poacic acid were normalized against the DMSO control conditions to define sensitivity or resistance of individual strains. To determine a p-value for each top sensitive and resistant mutant, we used the EdgeR package [21, 22]. A Bonferroni-corrected hypergeometric distribution test was used to search for significant enrichment of GO terms among the top 10 sensitive and resistant deletion mutants [23]. To understand the pathways that were most affected by poacic acid we developed a protein complex/pathway score based on the summation of the z-scores for each complex/pathway (Pathway z-score). Correlation of the chemical genomic profile of poacic acid with the yeast genetic interaction network to was done as described in Costanzo et al. (2010) [10].

MoBY-ORF Profiling:

MoBY-ORF profiling of GVL was conducted by first generating a pooled collection of the yeast GLBRC-Y133 containing the plasmid collection. The plasmid pool for transformation was generated as described previously (HO). For yeast transformation, the plasmids were extracted from 150 mL of *E. coli* culture MAXI Prep. Plasmid was used to transform GLBRC-Y133 via high efficiency LiAc transformation. Transformed yeast were plated to YPD+Geneticin (G418) agar plates and incubated until colonies appeared. A total of 50,000 colonies were washed from the plates using 1×PBS, mixed 1:1 with 50% glycerol, and stored until use. For MoBY-ORF profiling, 25 mL of media containing YPD+2.5% GVL+G418 was allowed to degas overnight in an anerobic chamber, and then inoculated with 100 μL of the transformed yeast pool (n=3). Cells were grown in culture for 48 hours. Genomic DNA was extracted from 1 mL from each culture using modified mini-prep with with zymolyase and glass beads. Gene specific barcodes were amplified, processed, sequenced, and analyzed as described above.

Growth and Sugar Conversion Experiments:

6 25-mL anaerobic flasks were prepared with Synthetic hydrolysate (SynH) (6% glucose/3% xylose)+1% GVL, pH 5.0. Flasks were inoculated with rinsed 133 or 133 pad1Δfdc1Δ cells to bring the initial OD to approximately 0.1. The tubes were grown for 72 hours with agitation anaerobically at 30° C. 1 mL samples were taken every 24 hours. Initial and daily samples were measured for OD and submitted for HPLC analysis to quantify sugar consumption and ethanol production.

Cell Leakage Assays:

A FungaLight™ cell viability assay (Invitrogen L34952) was used to determine if poacic acid caused membrane damage we used using a Guava Flow Cytometer (Millipore, USA). The population of stained cells (damaged integrity) vs non-stained cells can be determined by flow cytometry. Caspofungin (50 ng/ml) was included as a positive control. MMS and DMSO were included as a non-cell wall targeting and solvent control respectively. To test the effects of the compounds on both active and arrested cells, log-phase cultures were washed with 1×PBS and resuspended to an OD of 0.5 in either YPD media or YP (no carbon source) in the presence of the drugs (n=3) for 4 hours at 30° C. The cells were then stained and immediately read by flow cytometry. A one-way ANOVA and Tukey's test was used to calculate the difference between drug treatments among cells with arrested growth.

Synergy Screening:

To test for synergy, a 6×6 dose matrix was initially used to identify potentially synergistic dose combinations, these points were then confirmed in triplicate. 200 μl cultures were grown with combinations of with poacic acid (125 μg/ml), caspofungin (12.5 ng/ml) and fluconazole (3.8 μg/ml) and the relevant single agent and solvent controls their OD measured after 24 h. Synergy was determined by comparing actual optical density in the presence of compound combinations to an expected value calculated using the multiplicative hypothesis. This assumes that, in the absence of an interaction, each compound would decrease the OD of the cell culture by the same fraction in the presence of the other compound as it does when applied alone, i.e., $E=A*B/C$, where E is the expected OD, A is OD when compound A is applied alone, B is OD when compound B is applied alone, and C is OD of the control culture (DMSO). In the presence of synergy, the actual OD value is lower than the expected OD. A paired t-test was used to confirm statistical significance of this difference in 3 replicates of the experiment.

Determination of Ferulate and Diferulates by RP-HPLC-HR/AM-MS in Hydrolysates:

ACSH samples were diluted 1:10 and 20 μL samples were analyzed by reverse phase (C18) HPLC—high resolution/accurate mass spectrometry. Peak areas of peaks matching in retention time and accurate mass+/−10 ppm of authentic reference standards were used to calculate concentrations by comparison to an external standard curve.

GVL Synergy Experiments:

The synergistic interaction between GVL and ethanol was initially discovered using a 6-point dose matrix of the two compounds. We identified the points of the greatest synergy and perform triplicate growth curves of GLBRY-128 using a TECAN M1000 microplate reader. To confirm the GVL-R1 strain was less sensitive to the synergism between GVL and ethanol, used a 6-point dose matrix as described above with both GLBRCY-128 or GVL-R1 in a TECAN microplate reader for 48 hours at 30° C. Data from the most synergistic combination is presented (2% GVL-5% ethanol).

REFERENCES

1. Ho et al., Combining functional genomics and chemical biology to identify targets of bioactive compounds. *Curr Opin Chem Biol* 2011, 15:66-78.
2. Piotrowski et al., Death by a thousand cuts: the challenges and diverse landscape of lignocellulosic hydrolysate inhibitors. *Front Microbiol* 2014, 5.
3. Palmqvist and Hahn-Hägerdal, Fermentation of lignocellulosic hydrolysates. II: inhibitors and mechanisms of inhibition. *Bioresour Technol* 2000, 74:25-33.
4. Keating et al., Aromatic inhibitors derived from ammonia-pretreated lignocellulose hinder bacterial ethanologenesis by activating regulatory circuits controlling inhibitor efflux and detoxification. *Microb Physiol Metab* 2014, 5:402.
5. Almeida et al., Increased tolerance and conversion of inhibitors in lignocellulosic hydrolysates by *Saccharomyces cerevisiae*. *J Chem Technol Biotechnol* 2007, 82:340-349.
6. Luterbacher et al., Nonenzymatic Sugar Production from Biomass Using Biomass-Derived γ-Valerolactone. *Science* 2014, 343:277-280.
7. Ouellet et al., Impact of ionic liquid pretreated plant biomass on *Saccharomyces cerevisiae* growth and biofuel production. *Green Chem* 2011, 13:2743.
8. Docherty et al., Toxicity and antimicrobial activity of imidazolium and pyridinium ionic liquids. *Green Chem* 2005, 7:185-189.
9. McNew et al., Gos1p, a *Saccharomyces cerevisiae* SNARE protein involved in Golgi transport. *FEBS Lett* 1998, 435:89-95.
10. Costanzo et al., The genetic landscape of a cell. *Science* 2010, 327:425-431.
11. Cosson et al., Delta- and zeta-COP, two coatomer subunits homologous to clathrin-associated proteins, are involved in ER retrieval. *EMBO J* 1996, 15:1792-1798.
12. Clausen et al., PAD1 encodes phenylacrylic acid decarboxylase which confers resistance to cinnamic acid in *Saccharomyces cerevisiae*. *Gene* 1994, 142:107-112.
13. Mukai et al., PAD1 and FDC1 are essential for the decarboxylation of phenylacrylic acids in *Saccharomyces cerevisiae*. *J Biosci Bioeng* 2010, 109:564-569.
14. Magtanong et al., Dosage suppression genetic interaction networks enhance functional wiring diagrams of the cell. *Nat Biotechnol* 2011, 29:505-511.
15. Parreiras et al., Engineering and Two-Stage Evolution of a Lignocellulosic Hydrolysate-Tolerant *Saccharomyces cerevisiae* Strain for Anaerobic Fermentation of Xylose from AFEX Pretreated Corn Stover. *PLoS ONE* 2014, 9:e107499.
16. Sato et al., Harnessing genetic diversity in *Saccharomyces cerevisiae* for improved fermentation of xylose in hydrolysates of alkaline hydrogen peroxide pretreated biomass. *Appl Environ Microbiol* 2013:AEM.01885-13.
17. Fung S-Y et al., Unbiased screening of marine sponge extracts for anti-inflammatory agents combined with chemical genomics identifies girolline as an inhibitor of protein synthesis. *ACS Chem Biol* 2013.
18. Parsons et al., Exploring the mode-of-action of bioactive compounds by chemical-genetic profiling in yeast. *Cell* 2006, 126:611-625.
19. Andrusiak K: Adapting *S. cerevisiae* Chemical Genomics for Identifying the Modes of Action of Natural Compounds. Thesis; 2012.
20. Smith et al., Quantitative phenotyping via deep barcode sequencing. *Genome Res* 2009, 19:1836-1842.
21. Robinson et al., Design and analysis of bar-seq experiments. *G3 GenesGenomesGenetics* 2014, 4:11-18.
22. Robinson et al., edgeR: a Bioconductor package for differential expression analysis of digital gene expression data. *Bioinforma Oxf Engl* 2010, 26:139-140.
23. Boyle et al., GO::TermFinder—open source software for accessing Gene Ontology information and finding significantly enriched Gene Ontology terms associated with a list of genes. *Bioinformatics* 2004, 20:3710-3715.

We claim:

1. A recombinant yeast that has been genetically engineered to: ferment xylose and exhibit a reduced amount of functional PAD1 polypeptide, wherein the recombinant yeast has increased tolerance to gamma valerolactone (GVL) toxicity relative to a wild-type yeast or another recombinant yeast having the same genetic background but not exhibiting a reduced amount of functional PAD1 polypeptide.

2. The recombinant yeast of claim 1, further exhibiting a reduced amount of functional FDC1 polypeptide, wherein the recombinant yeast has increased tolerance to GVL toxicity relative to a wild-type yeast or another recombinant yeast having the same genetic background but not exhibiting reduced amounts of functional PAD1 and FDC1 polypeptides.

3. The recombinant yeast of claim 1, wherein the recombinant yeast comprises a disabling mutation in a gene encoding PAD1 polypeptide.

4. The recombinant yeast of claim 2, wherein the recombinant yeast further comprises a disabling mutation in a gene encoding FDC1 polypeptide.

5. The recombinant yeast of claim 3, wherein the PAD1 polypeptide is SEQ ID NO:8.

6. The recombinant yeast of claim 4, wherein the FDC1 polypeptide is SEQ ID NO:10.

7. The recombinant yeast of claim 1, further exhibiting reduced or undetectable amounts of functional ISU1, GRE3, and IRA2 polypeptides, wherein the recombinant yeast is capable of increased aerobic or anaerobic xylose fermentation relative to a wild-type yeast or another recombinant yeast not exhibiting reduced amounts of functional PAD1, ISU1, GRE3, and IRA2 polypeptides.

8. The recombinant yeast of claim 1, further comprising a disabling mutation at each of loci isu1, gre3, and ira2, whereby the mutations result in reduced amounts of functional ISU1, GRE3, and IRA2 polypeptides, respectively.

9. The recombinant yeast of claim 8, wherein the disabling mutation at the gre3 locus comprises a substitution of a threonine for the alanine at amino acid residue position 46 of SEQ ID NO:4; wherein the disabling mutation at the ira2 locus comprises a substitution of a stop codon for the glutamate at amino acid residue at position 2927 of SEQ ID NO:2; and wherein the disabling mutation at the isu1 locus comprises a substitution of a tyrosine for the histidine at amino acid residue position 138 of SEQ ID NO:6.

10. The recombinant yeast of claim 8, wherein the recombinant yeast produces ethanol at an increased rate relative to a wild-type yeast or another recombinant yeast not exhibiting reduced or undetectable amounts of functional ISU1, GRE3, and IRA2 polypeptides.

11. The recombinant yeast of claim 10, wherein the increased rate of ethanol production occurs under anaerobic conditions.

12. The recombinant yeast of claim 1, wherein the recombinant yeast is of the genus *Saccharomyces*.

13. The recombinant yeast of claim 12, wherein the recombinant yeast is of the species *Saccharomyces cerevisiae*.

14. The recombinant yeast of claim 3, wherein a portion of an extrachromosomal vector stably maintained in the recombinant yeast comprises the disabling mutation.

15. The recombinant yeast of claim 3, wherein a nucleic acid sequence comprising the disabling mutation is integrated into a chromosome of the recombinant yeast.

16. A yeast inoculum, comprising: (a) a recombinant yeast of claim 1; and (b) a culture medium.

17. A method for fermenting cellulosic material into ethanol, comprising contacting a GVL-treated hydrosylate to the recombinant yeast of claim 1 or the yeast inoculum of claim 16 for a period of time sufficient to allow fermentation of at least a portion of the cellulosic material to ethanol, whereby the rate of fermentation of cellulosic material of the GVL-treated hydrosylate to ethanol is increased relative to the fermentation rate of a GVL-treated hydrosylate not contacted to the recombinant yeast or the yeast inoculum.

18. The method of claim 17, further comprising separating the ethanol from fermented cellulosic material.

19. The method of claim 17, wherein the GVL-treated hydrolysate comprises xylose.

20. The method of claim 17, wherein the recombinant yeast is *Saccharomyces cerevisiae*.

21. The method of claim 17, wherein the cellulosic material comprises lignocellulosic biomass.

22. The method of claim 21, wherein the lignocellulosic biomass comprises at least one material selected from the group consisting of agricultural residues, wood, municipal solid wastes, paper and pulp industry wastes, and herbaceous crops.

* * * * *